(12) United States Patent  (10) Patent No.: US 7,783,094 B2
Collins et al.  (45) Date of Patent: Aug. 24, 2010

(54) SYSTEM AND METHOD OF COMPUTER-AIDED DETECTION

(75) Inventors: Jeffrey Collins, Belfountain (CA); Karen Saghatelyan, Toronto (CA); Frederic Lachmann, Toronto (CA)

(73) Assignee: The Medipattern Corporation, Toronto (CA)

( * ) Notice: Subject to any disclaimer, the term of this patent is extended or adjusted under 35 U.S.C. 154(b) by 1083 days.

(21) Appl. No.: 11/445,259

(22) Filed: Jun. 2, 2006

(65) Prior Publication Data

US 2006/0274928 A1  Dec. 7, 2006

Related U.S. Application Data

(60) Provisional application No. 60/686,397, filed on Jun. 2, 2005, provisional application No. 60/738,999, filed on Nov. 23, 2005.

(51) Int. Cl.
*G06K 9/00* (2006.01)

(52) U.S. Cl. ....................................... 382/128

(58) Field of Classification Search ............. 378/4, 378/8, 15, 901; 250/363.04, 370.09; 382/100, 382/131, 224; 600/300
See application file for complete search history.

(56) References Cited

U.S. PATENT DOCUMENTS

| | | | |
|---|---|---|---|
| 5,235,510 A | | 8/1993 | Yamada et al. |
| 5,491,627 A | * | 2/1996 | Zhang et al. ................ 600/408 |
| 5,790,690 A | * | 8/1998 | Doi et al. .................... 382/128 |
| 5,828,774 A | | 10/1998 | Wang |
| 5,848,198 A | | 12/1998 | Penn |
| 5,984,870 A | | 11/1999 | Giger et al. |
| 6,054,990 A | * | 4/2000 | Tran ........................... 715/863 |
| 6,058,322 A | | 5/2000 | Nishikawa et al. |
| 6,091,841 A | | 7/2000 | Rogers et al. |
| 6,138,045 A | | 10/2000 | Kupinski et al. |
| 6,167,146 A | | 12/2000 | Rogers et al. |

(Continued)

FOREIGN PATENT DOCUMENTS

EP  0487110 A2  5/1992

(Continued)

OTHER PUBLICATIONS

Stavros, A. T. et al., "Solid Breast Nodules: Use of Sonography to Distinguish between Benign and Malignant Lesions", Radiology, 1995, 196:123-134.

*Primary Examiner*—Andrew W Johns
*Assistant Examiner*—Tahmina Ansari
(74) *Attorney, Agent, or Firm*—Sean X. Zhang; John R. S. Orange; Blake, Cassels & Graydon LLP

(57) ABSTRACT

The invention provides a system and method for computer-aided detection ("CAD"). The invention relates to computer-aided automatic detection of abnormalities in and analysis of medical images. Medical images are analyzed, to extract and identify a set of features in the image relevant to a diagnosis. The system computes an initial diagnosis based on the set of identified features and a diagnosis model, which are provided to a user for review and modification. A computed diagnosis is dynamically re-computed upon user modification of the set of identified features. Upon a user selecting a diagnosis based on system recommendation, a diagnosis report is generated reflecting features present in the medical image as validated by the user and the user selected diagnosis.

33 Claims, 20 Drawing Sheets

U.S. PATENT DOCUMENTS

| | | | |
|---|---|---|---|
| 6,263,092 B1 | 7/2001 | Roehrig et al. | |
| 6,301,378 B1 | 10/2001 | Karssemeijer et al. | |
| 6,477,262 B2 * | 11/2002 | Wang | 382/132 |
| 6,553,356 B1 | 4/2003 | Good et al. | |
| 6,577,752 B2 * | 6/2003 | Armato et al. | 382/131 |
| 6,697,506 B1 | 2/2004 | Qian et al. | |
| 6,748,044 B2 | 6/2004 | Sabol et al. | |
| 6,757,415 B1 | 6/2004 | Rogers et al. | |
| 6,763,128 B1 | 7/2004 | Rogers et al. | |
| 6,785,410 B2 * | 8/2004 | Vining et al. | 382/128 |
| 6,799,066 B2 | 9/2004 | Steines et al. | |
| 7,466,848 B2 | 12/2008 | Metaxas et al. | |
| 2003/0103665 A1 | 6/2003 | Uppaluri et al. | |
| 2004/0008876 A1* | 1/2004 | Lure et al. | 382/128 |
| 2004/0101181 A1 | 5/2004 | Giger et al. | |
| 2004/0120558 A1* | 6/2004 | Sabol et al. | 382/128 |
| 2004/0193036 A1 | 9/2004 | Zhou et al. | |
| 2004/0258291 A1 | 12/2004 | Gustafson | |
| 2004/0264749 A1* | 12/2004 | Skladnev et al. | 382/128 |
| 2005/0010445 A1* | 1/2005 | Krishnan et al. | 705/2 |
| 2005/0013471 A1 | 1/2005 | Snoeren et al. | |
| 2005/0049497 A1* | 3/2005 | Krishnan et al. | 600/437 |
| 2005/0059876 A1* | 3/2005 | Krishnan et al. | 600/407 |
| 2006/0241370 A1* | 10/2006 | Kramp et al. | 600/407 |
| 2007/0003124 A1* | 1/2007 | Wood et al. | 382/131 |
| 2007/0133852 A1* | 6/2007 | Collins et al. | 382/128 |

FOREIGN PATENT DOCUMENTS

| | | |
|---|---|---|
| JP | 2002-200048 | 7/2002 |
| JP | 2003-116838 | 4/2003 |
| JP | 2005-124617 | 5/2005 |
| WO | WO 02/094097 * | 11/2002 |
| WO | WO 2004/029851 A1 | 4/2004 |
| WO | WO 2005/079306 A2 | 9/2005 |

* cited by examiner

FIG. 7

SYSTEM AND METHOD OF COMPUTER-AIDED DETECTION

CROSS-REFERENCE TO RELATED APPLICATIONS

This application claims priority from U.S. Provisional Application No. 60/686,397 filed on Jun. 2, 2005 and U.S. Provisional Application No. 60/738,999 filed on Nov. 23, 2005 which are hereby incorporated by reference.

FIELD OF INVENTION

The invention relates generally to the field of computer-aided detection ("CAD") and analysis of abnormalities. In particular, the invention relates to automatic detection of abnormalities in and analysis of medical images and automated assessment thereof.

BACKGROUND OF INVENTION

With the emphasis on early detection of cancer, more and more people are taking part in early screening programs, such as mammography screening and in some parts of the world ultrasound screening for breast cancer. Some recent studies suggest that diagnostic breast ultrasonography may successfully help distinguish many benign from malignant solid lesions or nodules. For example, in "Solid breast nodules: use of sonography to distinguish between benign and malignant lesions," by Stavros, A. T., et al., Radiology 196:123-134, 1995 ("Stavros"), it was suggested that sonography may be used to accurately classify some solid lesions as benign, allowing imaging follow-up rather than biopsy. Stavros provides a general method of reviewing lesions by detecting and evaluating characteristics of sonographic images corresponding to a set of pre-defined characteristics and their description ("Stavros characteristics"). Such local characteristics may include local spiculation, local branch pattern, local duct extension and local micro-lobulation, among others.

In general, successful early detection of abnormalities and diagnosis of cancer requires a radiologist to successfully and correctly identify and evaluate characteristics of masses seen in individual medical images in order to distinguish benign from malignant solid nodules. Medical images are not limited to those obtained from mammography or ultrasound screenings namely X-ray images (or digitized X-ray images) or sonographic images, but may include medical images obtained from any suitable medical scanning device utilizing any underlying image acquisition technology. Some examples of such medical images include sonographic images, Doppler images, spectral Doppler images, X-ray images, computed tomography (CT) images, positron emission tomography (PET) images, PET-CT images and magnetic resonance imaging (MRI) images.

The experience and expertise of an examining radiologist plays an important role in correctly identifying the characteristics so that a well-informed diagnosis may be established. Computer-aided detection has become an increasingly essential problem-solving tool in detecting and diagnosing cancer and other diseases. Modem technology has been advancing in many different ways to aid a radiologist to automatically identify and evaluate a battery of characteristics of masses seen in medical images. For example, technology has been developed to aid a radiologist to automatically identify and evaluate sonographic characteristics, to distinguish benign features in medical images from sonographic findings of malignancy, and to combine individual benign findings and malignant findings to classify a nodule as either benign or malignant in order to make a diagnosis. It is also known to automatically detect and mark candidate lesion or potential abnormalities within the image and thereby assist radiologists in the interpretation of medical images. General availability or accessibility of digitized medical imaging further facilitates the computerized image processing and computer-aided detection.

However, while computerized pattern recognition has seen tremendous advances in the past decade or so, sometimes, a computer application may still have difficulty in identifying most or all abnormalities. It is desirable not to miss a malignant lesion in the early stage of disease. As a radiologist may not place too high a confidence in results of automated detection, biopsy may be ordered, which sometimes turn out to be unnecessary. Further, even if successful detection of all relevant characteristics in a medical image were possible, automated diagnosis may not always provide a correct diagnosis due to, for example, inadequacy or lack of sophistication of models underlying a diagnosis engine.

The foregoing creates challenges and constraints for all CAD systems for extracting, i.e., identifying characteristics and medical features in medical images and suggesting diagnosis based on characteristics automatically detected in the medical image. There is therefore a need for a CAD system and method as compared to the existing art. It is an object of the present invention to mitigate or obviate at least one of the above mentioned disadvantages.

SUMMARY OF INVENTION

The invention relates to computer-aided automatic detection and identification of abnormalities in and analysis of medical images. Computer assisted assessment of detected abnormalities is also provided. Features within a medical image relevant to diagnosing diseases are identified and presented to a user for review. Advantageously, the medical image is first segmented to provide one or more segmentation candidates to facilitate further image processing. A segmentation candidate is confirmed or selected from the segmentation candidate or candidates, either manually by a user or automatically detected or identified by the system. The segmented medical image is analyzed to extract and identify features in the image relevant to a diagnosis, based on which the system computes an initial diagnosis by combining the identified features with a diagnosis model. The user is provided with an annotation tool to confirm or modify a list of identified features presented to the user. Upon modification of the list of features, a revised diagnosis is dynamically re-computed. Upon a user having selected a diagnosis, either confirming or modifying the computed diagnosis, a diagnosis report is generated reflecting the features present in the medical image as validated by the user and the diagnosis confirmed or modified by the user.

In a first aspect of the invention, there is provided a system for providing interactive computer-aided detection of abnormalities present in one medical image or multiple medical images. The system includes an image processor for processing a medical image and extracting features within the medical image relevant to diagnosing the abnormalities, the extracted features satisfying descriptions of a set of pre-defined features, a decision engine for generating a computed diagnosis from the extracted features, and an annotation and modification tool for a user to identify a set of features within the medical image aided with the extracted features and to establish a diagnosis based on the set of identified features and the computed diagnosis.

In one feature of this aspect of the invention, the plurality of rules are calibrated from a pool of diagnosed medical images. In another feature of this aspect of the invention, the system includes a lesion locator for analyzing the medical image and identifying a suspect lesion within the medical image. In yet another feature, the image processor segments the medical image, identifies a plurality of segmentation candidates of the medical image for user selection, and receives an indication from a user to process one of the segmentation candidates as a segmented image.

Optionally, a user is able to reject any of the displayed segmentation candidates and review the complete set of intermediate segmentation results leading to the displayed candidates with the objective of selecting another candidate, The user can also refine a selected candidate by modifying segmentation results, for example, by editing existing control points or defining additional control points on a segmentation outline, thereby obtain a modified segmentation outline.

In a second aspect of the invention, there is provided a system for providing interactive computer-aided detection of abnormalities captured in a medical image. The system includes a display for presenting the medical image; input devices for receiving user input; an analytic engine for identifying image characteristics from the medical image and providing an initial set of identified image characteristics for user review; and an annotation and modification tool for a user to modify said initial set of identified image characteristics to obtain a modified set of identified image characteristics. The system computes an initial diagnosis from the initial set and a set of pre-defined criteria, provides the initial set and the initial diagnosis to the user for review, receives the modified set from the user, and re-computes a diagnosis from the modified set and the set of pre-defined criteria for user validation.

In another aspect of the invention, there is provided a system for providing computer-aided diagnosis of abnormalities in a plurality of medical images. The plurality of medical images are different views of a region of a patient's body. The system includes an image acquisition module for acquiring the plurality of medical images, an image processor for processing each of the plurality of medical images and identifying an initial set of features within the each medical image relevant to diagnosing the abnormalities, a decision engine for computing an initial diagnosis from the plurality of the initial sets of identified features, and an annotation and modification tool for a user to modify the initial set of identified features to obtain a modified set of identified features. The decision engine re-computes a computed diagnosis for user validation from the modified set of identified features.

In one feature of this aspect of the invention, the system is configured for processing medical images obtained from multiple modalities. These multiple modalities include at least two of sonographic images, Doppler images, spectral Doppler images, X-ray images, CT images, PET images, PET-CT images and MRI images.

In yet another aspect of the invention, there is provided a method of providing interactive computer-aided detection of abnormalities captured in a medical image. The method includes the steps of obtaining a digitized medical image; processing the digitized medical image to identify an initial set of image features within the digitized medical image, the initial set of identified image features satisfying descriptions of a set of predefined characteristics; providing the initial set of identified image features for user review; receiving a modified set of image features modified by the user from the initial set of identified image features; computing a diagnosis from the modified set for user validation; and producing a diagnosis report upon receiving a validated diagnosis from the user.

In yet another aspect of the invention, there is provided a method of acquiring a medical image aided by a computer-aided detection system, the computer-aided detection system having a medical imaging device for generating a medical image and an analytic engine for processing the medical image, the method includes the steps of acquiring a plurality of medical images from a patient using the medical imaging device, analyzing each of the plurality of medical image using the analytic engine; and adjusting acquisition conditions to obtain an optimal image from the plurality of medical images.

In other aspects the invention provides various combinations and subsets of the aspects described above.

BRIEF DESCRIPTION OF DRAWINGS

For the purposes of description, but not of limitation, the foregoing and other aspects of the invention are explained in greater detail with reference to the accompanying drawings, in which:

FIG. 7 shows an exemplary screen display that a radiologist may use for modifying and saving a summary text on findings generated from a build-in template and results shown in FIG. 6;

FIGS. 8A and 8B show steps of a workflow implemented by the software system shown in FIG. 2, wherein FIG. 8A shows the first half of the workflow and FIG. 8B shows the second half;

DETAILED DESCRIPTION OF THE INVENTION

Figure 1:
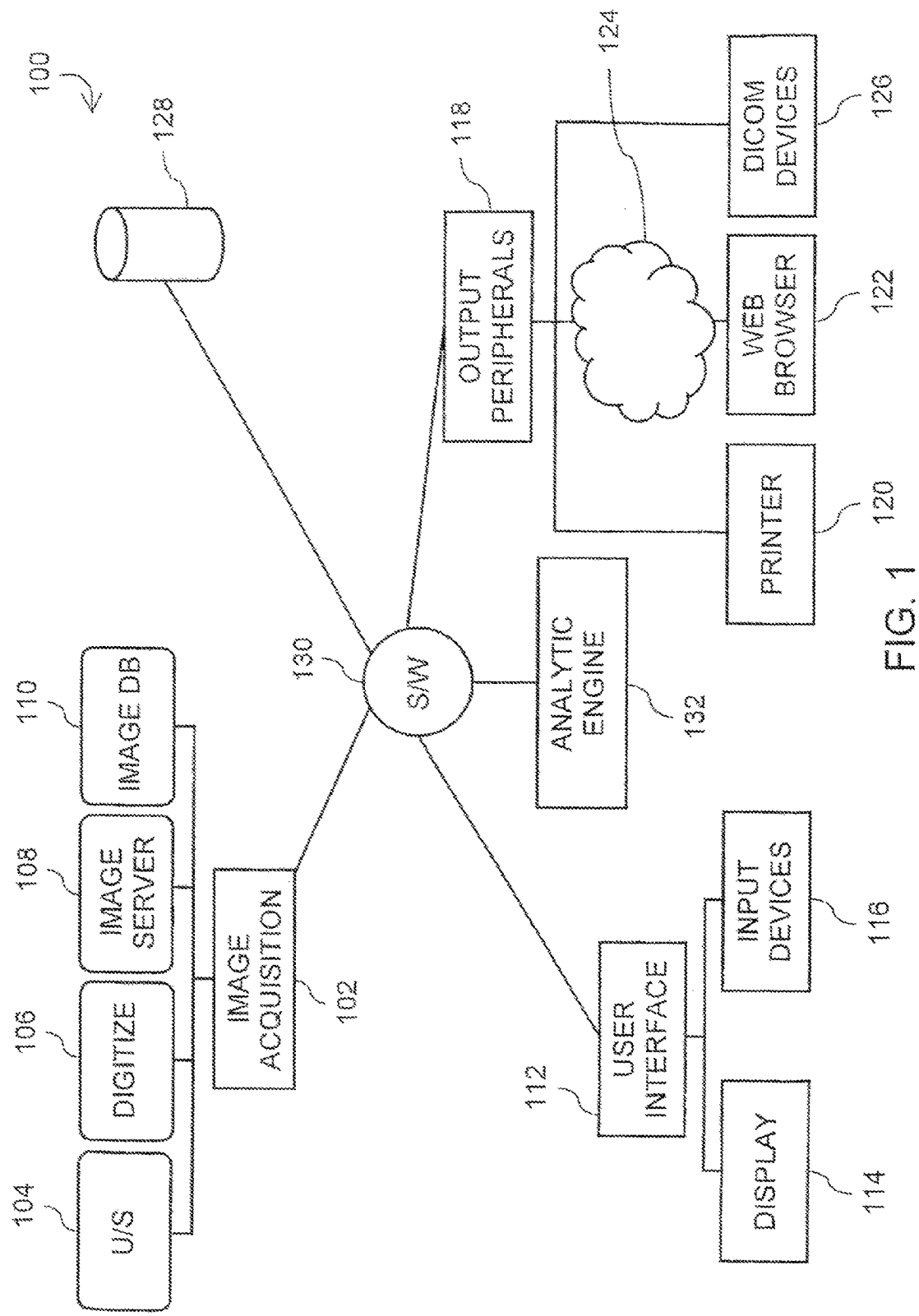
FIG. 1 is a schematic diagram showing a CAD system that implements an embodiment of the present invention.

The description which follows and the embodiments described therein are provided by way of illustration of an example, or examples, of particular embodiments of the principles of the present invention. These examples are provided for the purposes of explanation, and not limitation, of those principles and of the invention. In the description which follows, like parts are marked throughout the specification and the drawings with the same respective reference numerals.

FIG. 1 shows a CAD system 100 that is controlled by a software system for automatically analyzing medical images, detecting, identifying and classifying physical, textural and morphological characteristics or other features of masses within medical images, providing computer-aided detection and assessment of suspected lesions for user selection, and allowing interactive feedback from a user to dynamically modify a list of detected features and the diagnosis computed therefrom. The user may be a technician, a radiologist, or a physician. The user may also be an operator of the CAD system 100, for example, a staff member, who receives instructions from a radiologist or a physician from a remote location. The CAD system 100 may be used by a user to acquire medical images from a medical scanning device and analyze the images in real-time. The user may also load a previously acquired medical image from a database for further analysis. Alternatively, a user, such as a radiologist or physician, may share an image, whether acquired in real-time or previously acquired, with other radiologists or physicians to collectively evaluate and analyze the image and establish a diagnosis.

The CAD system shown in FIG. 1 has an image acquisition subsystem 102. The image acquisition subsystem 102 can acquire medical images in real-time when connected to one or multiple medical image scanning devices. The CAD system provides in general a multi-modality platform. Which modality is selected depends on the image type. For example, the system may be implemented or configured to support ultrasound images, X-ray images, or CT, PET, PET-CT, Nuclear, MRI images, or images from other imaging modalities that is connected to the CAD system. The system itself may also be included in a console or workstation for review of some or all medical imaging modalities.

In one implementation, the image acquisition subsystem is connected to a medical scanning device 104 for acquiring medical images from a patient in real-time. As noted, the medical scanning device 104 can be an ultrasound machine that includes an ultrasonic source and a transducer or transducers. The medical scanning device may also be X-ray based, consisting of an X-ray source and an X-ray imager. The medical scanning device may also be a CT, PET, Nuclear or MRI scanner. Any suitable imaging device for acquiring medical images of a patient's tissue, bones or organs may be used.

The image acquisition subsystem 102 may also load previously acquired images for further study or for sharing with other users, such as radiologists, technician or physicians. For example, the image acquisition subsystem 102 may include a digitizer 106 for digitizing a previously acquired image that is recorded on a film. Alternatively, the image acquisition subsystem 102 may retrieve an image from a remote image server 108 or from an image database 110 accessible to the CAD system The CAD system 100 includes a user interface 112 that allows a user of the system to view an image, to manipulate its presentation, and to interact with the system. The user interface 112 includes a display 114. The display 114 may be a monitor, a projector, or any other suitable display device that is capable of visually presenting a medical image to the user and is capable of presenting graphical and textual contents. The user interface 112 also includes input devices 116 for the user to interact with the system and to identify to the system particular regions of interest in the displayed medical image. The input device 116 may include a keyboard, for example, for the user to enter any textual input. A voice recognition module may be provided for voice-to-text transcription. It may also include a mouse or some other pointing device for the user to identify a particular pixel or region of the medical image to the system. Display 114 and input device 116 may be physically combined into a single piece of hardware unit, such as a touch screen that is capable of both displaying graphic and textual output and receiving user input.

The system 100 also provides a number of output peripherals 118. A user may use the output peripherals 118 to reproduce or record results of an analysis session or other output of the system. For example, the output peripherals may include a printer 120. The printer may be, for example, film based or paper based. A film-based printer may be used to transfer the medical images, either the original image or the processed image to a film for use with more traditional display devices that require a filmed image. A paper-based printer may also be used to produce hard copy reports for sharing with other physicians or for archiving purposes. The output peripherals 118 may also include a web browser 122, for sharing results with other radiologists or physicians over a telecommunication network 124. The telecommunication network 124 may be a local area network (LAN) or the Internet. This allows a physician to remotely review images obtained by an operator from a patient and make any modification in real-time to results automatically produced by the system 100. In addition, the output peripherals 118 may include DICOM-compliant devices 126 for transferring or storing processed results, namely composite images generated by the system together with associated reports.

The system 100 has a data warehouse 128. The data warehouse may include its own modules for retrieving and managing data, or may simply provide storage space for storing data therein. The data warehouse 128 is generally for storing system related or generated data, including archiving processed medical images. For example, the data warehouse 128 may be used for storing pre-diagnosed images, modeling parameters, and other pertinent data used by the system for providing automated detection. Preferably, the data warehouse 128 supports archiving DICOM-compliant images but other forms of images such as JPEG, BITMAP etc. may also be processed. Annotations, comments, results of image processing all can be archived as part of a DICOM-compliant file. Audit information, such as user ID, date or time stamp of processed images, and user addition or modification of detected features all can be recorded for each archived instance of a processed image, as well.

Figure 2:
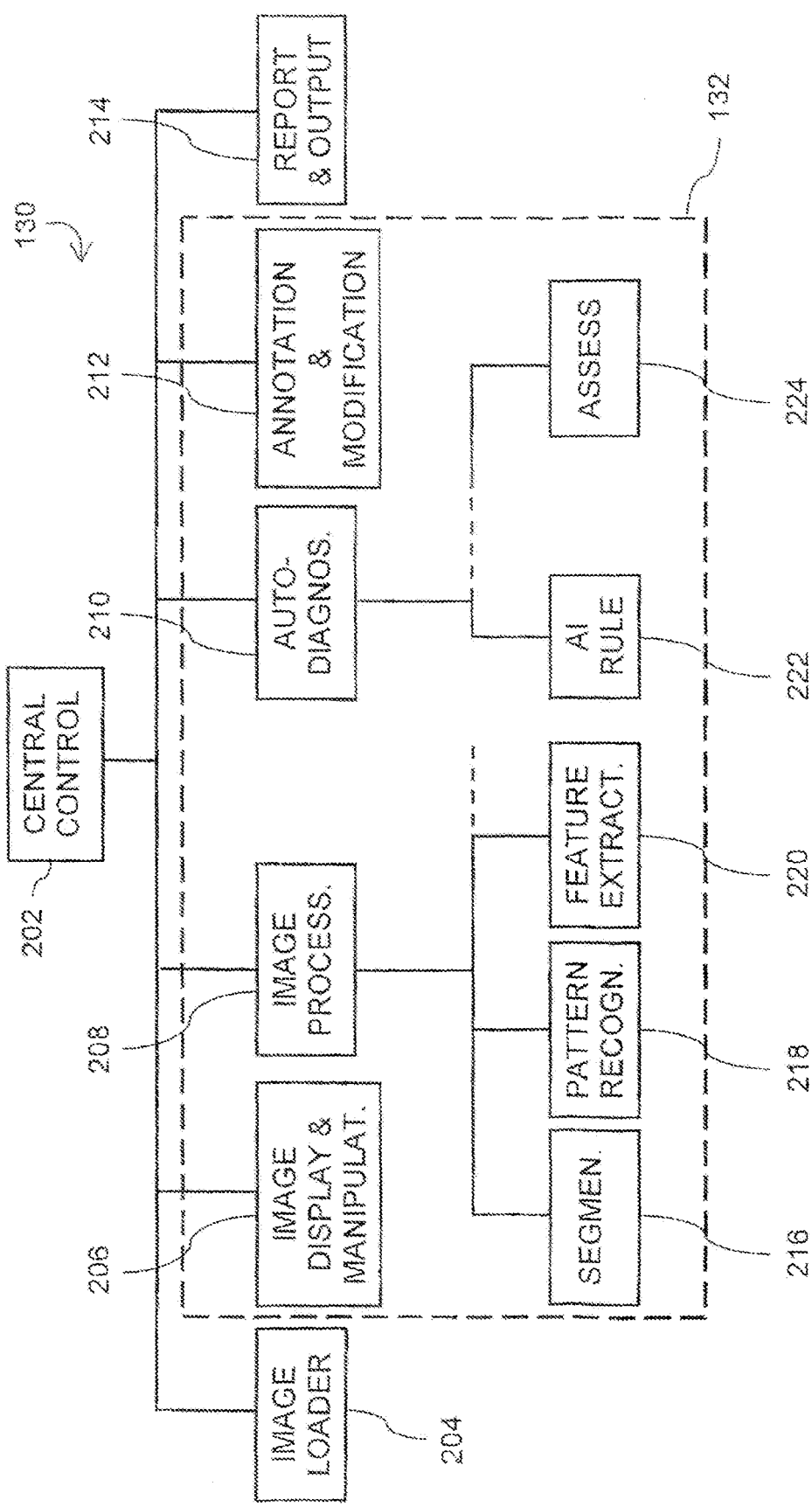
FIG. 2 illustrates schematically functional components and architecture of a software system for controlling the CAD system shown in FIG. 1.

The system 100 shown in FIG. 1 is controlled by a software system 130. Referring to FIG. 2, software system 130 coordinates and controls the flow of data and the processes implemented by the CAD system 100. The software system 130 has a number of components. These software components do not have to reside in a single computer hardware unit. They may be dedicated software systems stored at different locations and executing on different processors of the hardware units, or even as independent modules executing on different computers. The software components can also be provided by different manufacturers. For example, a medical scanning device manufacturer may provide its own software component for image processing or feature extraction. These software components can be combined together to provide the functionality of system 100 as described herein. These software components may also be combined in such a way as to form different subsystems to deliver dedicated sub-functionalities. For ease of convenience, in the following, these software components will be considered conceptually as part of the software system 130 that has all of its components stored on one computer readable medium, such as a hard disk, and executing on one processor. As will be appreciated, the CAD system provides in general a multi-modality platform. This may be achieved, for example, by providing a modality-specific component in each component of the software system 130, where required, to implement the supported modalities.

The software system 130 has an analytical engine 132 for analysing medical images and deriving a diagnosis for user review and validation. For example, in one implementation, the analytical engine 132 processes images obtained by the image acquisition subsystem 102 to identify regions of interests for further feature extraction, extracts features presented in an image, such as physical or morphological characteristics, prepares the resulting information for display and review, and maps the set of detected features to a diagnosis for user review and confirmation.

FIG. 2 shows schematically components of the software system 130. The software system 130 has a central control module 202 for controlling and coordinating data flow between and processes of various component modules of software system 130. Software system 130 has individual modules for interacting, directing and monitoring corresponding hardware units or subsystems. Its image loader 204 interacts with and directs the operation of image acquisition subsystem 102 of the CAD system 100. Conceptually part of the analytical engine 132, an image display and manipulation module 206 is provided for a user to adjust and manipulate the display of images. Also provided as part of the analytical engine 132 are an image processing module 208, a decision module 210, and an annotation and modification module 212. A report module 214 is provided for producing reports and generating output.

When a medical image is required for processing or viewing, the image loader 204 directs the image acquisition subsystem 102 to load, i.e., to retrieve or obtain the medical image. Once the medical image is retrieved or obtained, the image display and manipulation module 206 sends the image to the display 114 for displaying the image to a user. The user can use the input devices 116 to further manipulate or adjust the display of the image on the display 114. A user may manipulate the displaying of image, for example, by changing its contrast, brightness level, or panning or zooming in or out of a particular region of the image. The user may also select a region of the image for further processing.

The image processing module 208 or image processor is responsible for pattern recognition and feature extraction and performs various computerized image processing and pattern recognition operations. The image processing module 208 computes, i.e., extracts and identifies physical, texture, morphological as well as modality-specific characteristics associated with a mass defined by the boundary of an abnormal region, such as a lesion or a nodule, that has been identified in a segmentation process. In general, the image processing module needs to be implemented or configured differently to process images obtained from different modalities. For example, when an ultrasound image is loaded, the features are generally those defined for ultrasound images. The features may be those associated with the interior of a suspect lesion as well as those identified from regions outside but adjacent the boundary of an abnormal region, such as posterior shadowing in an ultrasound image. The features to be extracted or identified are generally pre-defined and considered by the medical profession as being relevant to diagnosing diseases, such as cancer. The descriptions of these features are generally provided together with the definitions of these features. One such set of pre-defined characteristics and lexicon is that developed by American College of Radiology (ACR) for use with Breast Imaging Reporting and Data systems (BI-RADS®). For different applications, different pre-defined sets and standards may be used. For example, as part of a standard, BI-RADS lexicon is primarily used for radiology, while the Bethesda System for Reporting Cervical Cytologic Diagnoses is primarily used for cytology. It will be understood that while the examples provided herein relate to diagnosing cancer, they are for illustration only and the system and the process and method described herein are applicable to diagnosing diseases in general, and not restricted to diagnosing cancer.

The required image processing operations may include segmentation (i.e., selecting and delineating a region of an image for further study and processing), pattern recognition (i.e., analyzing and classifying patterns in an image) and feature extraction (i.e., analyzing and identifying features or characteristics that may be relevant to diagnosing abnormal or normal conditions in the tissues represented by the image). FIG. 2 shows three modules for segmentation, pattern recognition and feature extraction, though it will be appreciated that other modules may be included for other image processing needs.

Figure 3A:
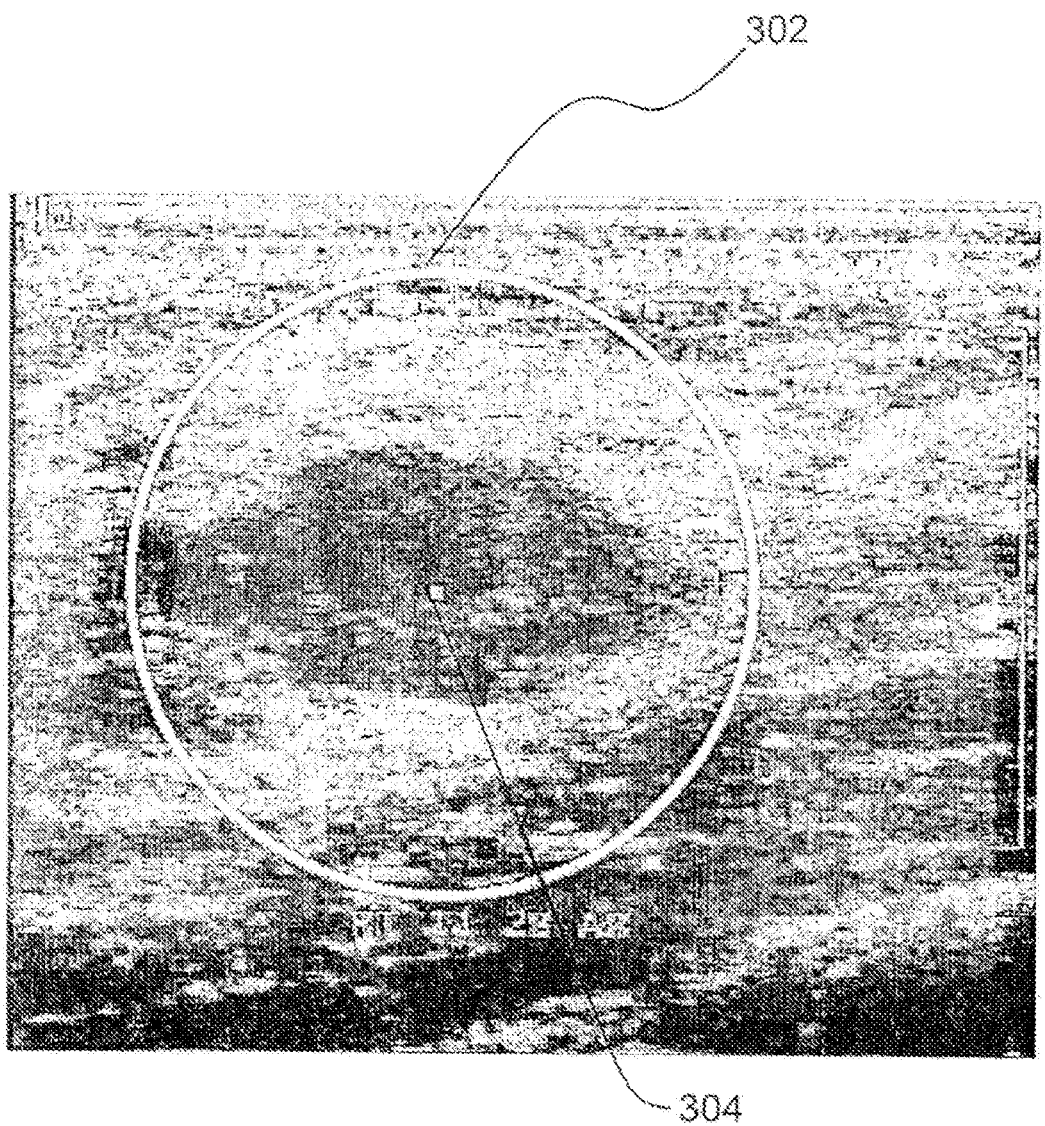
FIG. 3A shows an exemplary screen display presented to a user by the system shown in FIG. 1, from which the user can select an initial segmentation candidate and define a region of interests ("ROI") for further study.

The image processing module 208 is shown to have a segmentation module 216. The segmentation module 216 analyzes a region of interest ("ROI") identified by a user and delineates the boundary of an abnormal region such as a nodule within the ROI. The ROI may be identified manually by a user, or automatically by the system and suggested to a user. In one implementation, the user selects and identifies the ROI to the system by first selecting a segmentation "seed point", i.e., a point in the interested region. FIG. 3A shows an exemplary screen display from which a user may select an ROI. Typically, the seed point 302 is selected at a point near the general center of the interested region, such as a suspected solid nodule. The user may select the segmentation seed point by, for example, using a mouse and clicking a point in the central region of the nodule (see FIG. 3A). ROI is defined by selecting the seed point and dragging the cursor away from that point. A circle appears constraining the region into which the segmentation algorithm shall work The user releases the mouse button until the ROI 304 is sufficiently large as to enclose the entire nodule.

Figure 3B:
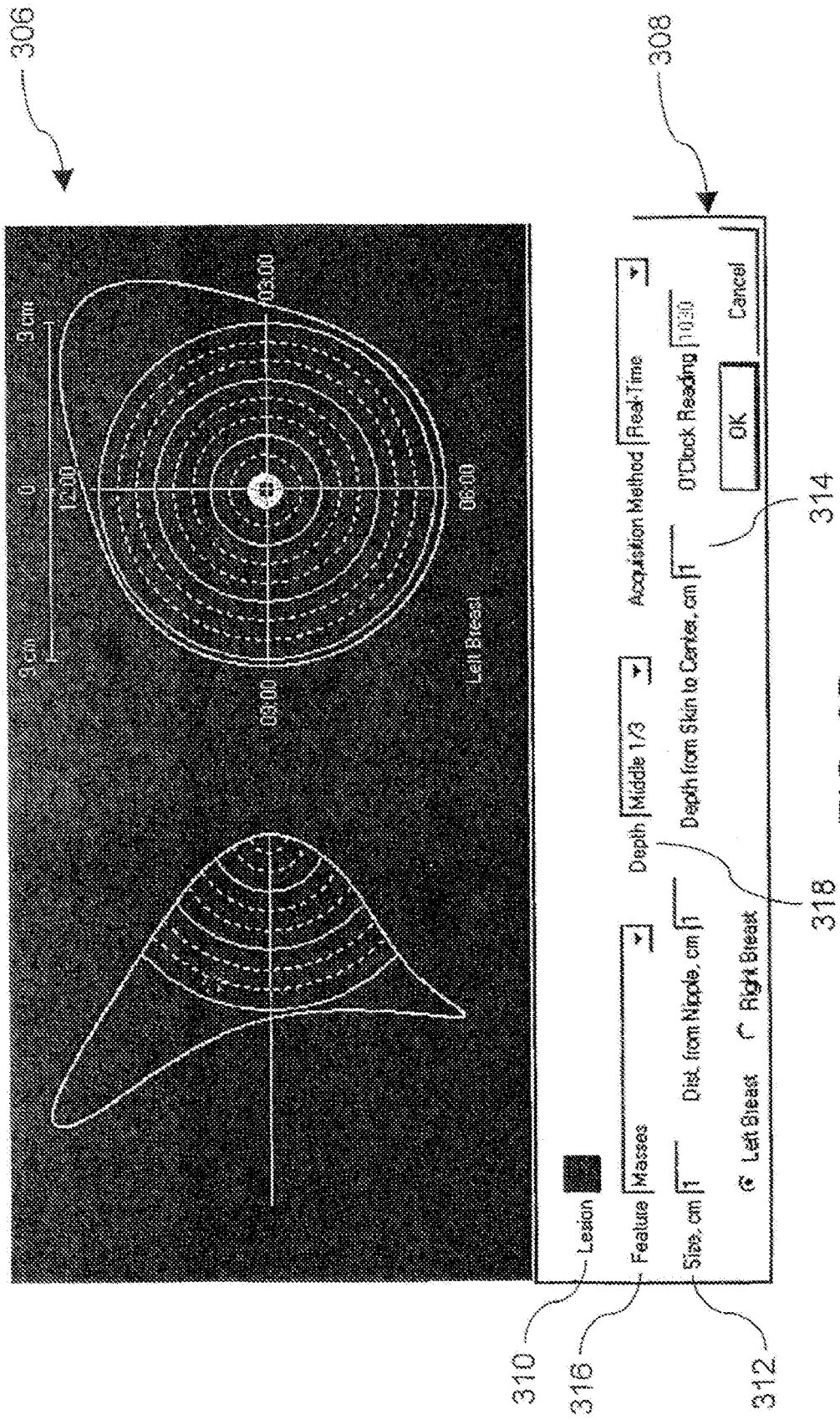
FIG. 3B shows another exemplary screen display for a user to enter identification parameters to define a region of interests for further study.

Alternatively, a user may identify the ROI by providing a set of coordinate values of the "seed point" and an estimated size of the lesion. This approach may be further refined, where the lesion appears to be an elongated mass, by providing an orientation of an axis generally aligned with the elongated mass and an aspect ratio. FIG. 3B shows a location identification window 306 for a user to enter lesion identification parameters 308, which may include, for example, any one of a lesion identification number 310, a lesion size parameter 312, lesion coordinates 314, a lesion feature indicator 316, a lesion depth indicator 318, among others, and a combination thereof. Here, the lesion identification number 310 refers to an identification number, for example, a first lesion, a second lesion, a third lesion, and so on, among several lesions identified in the image. The lesion size parameter 312 provides an estimate of the lesion size, for example, 1 cm. The location of the lesion may be defined using a suitable coordinate system through lesion coordinates 314, such as depth from skin, distance from nipple and azimuth angle from a vertical direction. The lesion feature indicator 316 refers to a feature type, for example, features related to mass, shape, orientation, calcification of a suspect lesion, among others. The lesion depth indicator 318 provides an estimate of a depth of the lesion from skin as a relative measure, e.g., relative to the size of breast base.

Advantageously, once a suspect lesion is identified, the image may be segmented to delineate a boundary contour of the suspect lesion, or segmentation outline. This may facilitate further image processing, as image patterns and features relevant to a diagnosis of the suspected lesion are more likely those inside or outside but adjacent the segmentation outline. Different algorithms may be implemented for segmenting an ROI. For example, in one implementation, a front propagation type of region growing algorithm is implemented for segmenting lesions in an ultrasound image. A "seed point" within the suspect lesion is first selected. Adaptive thresholds are selected for determining the boundary outline. Region growing from seed point based on adaptive thresholds may further take into account local information and is constrained by domain knowledge. Initial region outlines are defined based on local information. When equilibrium is reached, defined region outlines are refined by deformable model driven by domain constraints. It will be appreciated that any suitable algorithm can be used for segmenting an ROI. Different applications may require different suitable algorithms. For example, algorithms best suited for segmenting images for diagnosing breast cancer may not be optimal for segmenting images obtained from a CT scan; as another example, a segmentation algorithm developed for ultrasound images will need to be re-tuned and/or modified to process MRI data.

Each algorithm can produce several segmentation candidates, i.e., segmentation outlines that may correctly delineate the suspect lesion. Based on certain pre-established criteria, the system can present one as the best candidate and the rest as second-best candidates. The segmentation module 216 may present only the best candidate produced by the most suitable algorithm. Preferably, the segmentation module 216 presents the best candidate along with several second-best candidates for user selection. Where several algorithms are available, candidates identified by other algorithms may also be presented for user selection.

Figure 4A:
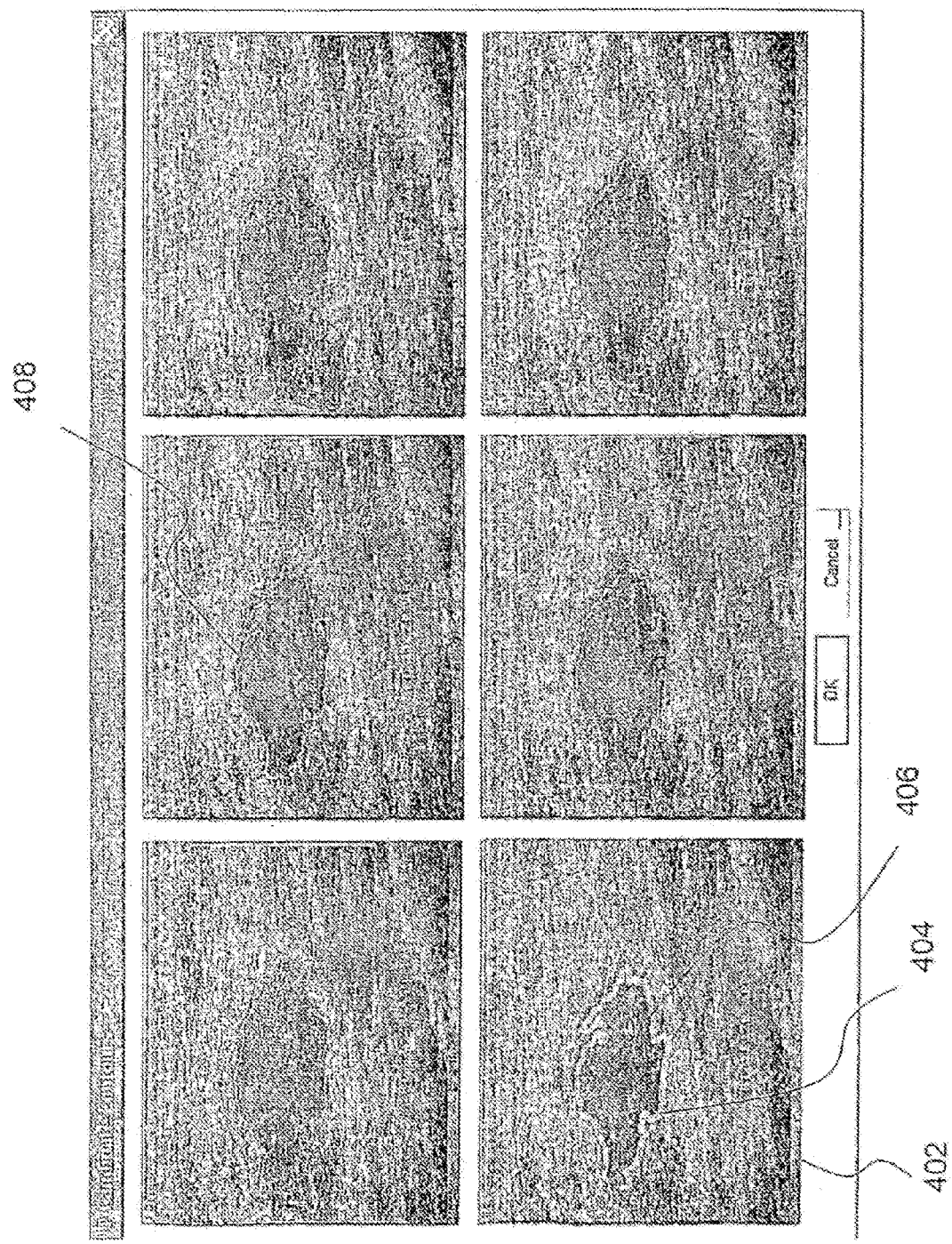
FIG. 4A shows an exemplary screen display presented to a user by the system of FIG. 1, from which the user may select one of several segmentation candidates for further processing and study.

In one implementation, the segmentation module 216 presents for user selection 6 segmentation candidates in a temporary window, as shown in FIG. 4A. Each candidate image 402 is a composite image with the original image superimposed thereon a possible lesion boundary 404. What is considered the best candidate 406 of the segmentation process is identified, e.g., by highlighting it, and made active for further processing. Along with the best candidate 406 are displayed several second-best results 408. Only these six candidates, instead of all segmentation candidates, are provided to the user for selection. A user may select one the system determined to be the best result. The user may also select a segmented image from one of the other candidate images 408. The user may identify a selection to the system by, for example, double-clicking a segmentation candidate. Optionally, a user can reject any or all of the displayed candidates and review the complete set of segmentation results. This allows the user to visually examine all segmentation results and pick one suitable candidate based on the user's own experience and judgment. Alternatively, the system may also be configured to select the best candidate generated using the most suitable algorithm for further processing, without any user intervention.

The user can also refine a selected candidate by editing the segmentation outline 404. To do this, a user may edit existing control points or defining additional control points on a segmentation outline. The user may modify a displayed segmentation candidate by editing one or several control points 410 of the segmentation outline 404 to manually segment an ROI (see FIG. 4B). The user may also modify a displayed candidate by defining new control point(s). After the user finishes editing existing control point(s) or adding new control point(s), the system displays a modified segmentation outline for the user to confirm. Once the system receives a selection from the user, the system starts its computerized pattern recognition and feature extraction process.

The image processing module 208 shown in FIG. 2 has a pattern recognition module 218. Pattern recognition module 218 analyzes an image, in particular an ROI delineated by the segmentation module 216, to identify and index morphological and texture patterns or features in the image. Pixels both inside and outside the segmentation outline are scanned to identify patterns or local features of a suspect lesion and modality-specific features such as sonographic characteristics. Local characteristics such as local spiculation, local branch pattern, local duct extension and local micro-lobulation, may be identified. The segmentation outline itself also can be analyzed to identify features of the suspect lesion that may be relevant to the diagnosis. Patterns, local features, modality-specific characteristics, features identified from the segmentation outline, among other features, are compared with descriptions of a set of pre-defined features, such as sonographic characteristics defined by ACR-BIRADS lexicon or Stavros characteristics, to generate a list of features as identified from the set of the standard. Pattern recognition module 218 analyzes the image to identify these patterns and local features. Pattern recognition module 218 may also analyze the image to identify features such as clustering and contrast of pixels in a segmented ROI, or analyze the image to incorporate some notion of domain knowledge including surrounding information in order to better identify specific local features.

The image processing module 208 shown in FIG. 2 has a feature extraction module 220 for extracting from these locally identified patterns special features that may be relevant to diagnosing cancer. Some of these features may include shape, orientation, angular margin, lesion boundary, and calcification. The features may also include those unique to a specific detection technology. For example, for an ultrasonic image, the features may include echo patterns and posterior acoustic features.

In one implementation, the feature extraction module 220 detects features matching descriptions of a set of pre-defined sonographic characteristics combined with ACR-BIRADS lexicon. In other words, a feature is considered to be identified and detected if characteristics of an object in the image satisfy the corresponding description of the feature in the set of pre-defined characteristics. The feature extraction module 220 uses a set of pre-defined characteristics and the characteristics' description, for example, the ACR-BIRADS lexicon, to make automated feature identification and extraction. The feature extraction module 220 uses detection performance thresholds to determine if any feature can be identified from the indexed local characteristics recognized by the pattern recognition module 218. The indexed characteristics are each assigned a probability based on a goodness-of-fit indicator against the description of the matched feature, to provide a statistical measure of the likelihood of their presence in the image. A characteristic is considered to exist in the image or is detected when the probability is above that threshold. Conveniently, all characteristics may be assigned the same threshold. Preferably, these thresholds may be based on Stavros' performance thresholds obtained from calibrating a set of diagnosed images. Such thresholds then depend on each characteristics and are determined from the results of calibrating the set of already diagnosed images.

The software system 130 has a decision module 210 for computing an automated diagnosis or assessment and suggesting the computed diagnosis to a user. The decision module 210 examines all features identified, including properties such as the statistical likelihood each feature may present and the extent or size of the feature, ranks the importance of each feature relating to a diagnosis, and computes an assessment or diagnosis. In general, a range of discrete assessments are possible. The particular set of possible assessments depends on the standard used. For example, the assessment may be one of benign, malignant, or indeterminate, or may be one to which BI-RADS category the lesion belongs. In other words, the decision module 210 maps the findings, or set of features extracted, to an assessment of the lesion based on the underlying model. As will be appreciated, different models may be employed for assessing suspected lesions. The modality of the software system 130 permits different models to be applied to the same set of features extracted to arrive at an assessment. As will be further appreciated, the operation of the decision module 210 is independent of the feature exaction module 220. The decision module 210 will provide an automated assessment whether the set of features provided to it as input is automatically identified, entirely identified manually by a user, or a combination hereof. In other words, the decision module 210 may be considered as a sub-system that provides the dedicated sub-functionality, namely, computing an assessment, as mentioned earlier.

Different modules may be provided for providing different diagnosing functions. Assessments obtained by applying different models may not necessarily be the same. Results from different models are combined, preferably with appropriate weights, to arrive at a computed diagnosis. The decision module 210 in FIG. 2 is show to have an AI rule module 222 and an assessment module 224, though it will be understood that the modular design of the software system 130 allows the substitution or addition of diagnosis modules where desirable.

The AI rule module 222 makes use of knowledge gained in the past, such as from diagnosis of a pool of image data, the corresponding biopsy results and collective knowledge of radiologists and physicians. In one implementation, the knowledge is summarized as a set of artificial intelligence (AI) rules. From the set of AI rules, the findings made from pattern recognition and feature extraction can be mapped to an automated assessment. As will be described in detail later, not all features detected may be of equal importance. The importance of each detected and identified features will be incorporated in the set of AI rules. AI rule module 222 computes a preliminary diagnosis assessment based on the set of features detected and their relative importance to a particular diagnosis.

The following example outlines the steps of one method of producing a set of AI rules, in this case, to build a statistical model. A pool of diagnosed images, together with their corresponding biopsy results, is first selected. Characteristics identified from these images as well as the known diagnosed results are compiled. From these, data, a statistical model based on mutivariate adaptive regression splines (MARS) technology can be built, which has the general form $$Y = C0 + \Sigma Ci * BFi$$

where C0 and Ci are coefficients and BFi are the i-th basis functions. Each basis function takes as input a defined combination of defined set of characteristics and potentially defined set of basis functions. For example, a basis faction may have the form BF240=(ECHO=1 OR ECHO=3 OR ECHO=4 OR ECHO=5) * BF180 where ECHO is one sonographic category with multiple options (1, 3, 4 or 5). The form of the basis functions as well as the coefficients are obtained by fitting the model with the statistical data, namely the characteristics identified in the diagnosed images as well as the known diagnosed results associated with the diagnosed images.

Once such a model is built, it can be incorporated into the AI rule module 222 for computing a diagnosis, namely an overall likelihood that a lesion may be benign or malignant, based on the set of characteristics identified in the diagnosed images. It will be appreciated that the computation of an assessment is not limited to using a statistical model. The assessment may also be computed using a super vector machine (SVM) method or may be generated using an AI engine that employs a more complicated approach such as a neural network method. The modality of the system permits the incorporation and integration of different assessment engines into the system and the combination of the outputs of these different assessment engines where desirable.

Although an assessment may be provided in any manner, in general, the assessment module 224 provides a user with an assessment conforming with a common standard, such as providing a diagnosis as a BI-RADS assessment. A single assessment may be presented to a user as an automatically computed diagnosis. Preferably, a group of possible BI-RADS assessments is presented to a user. In one implementation, a user is presented with one of two groups of assessments: "benign" which corresponds to BI-RADS 1 to 3 and "malignant" which corresponds to BI-RADS 4a to 5. The user will then have to select a particular assessment from the suggested group of assessments or make an assessment selected from outside the suggested group. This tends to discourage adopting an automated diagnosis without evaluation by a user. Of course, other granularity of the grouping is possible. For example, the possible assessments may be divided into "benign", "intermediate, or possible benign", and "malignant."

After a diagnosis is computed, the decision module 210 may also tag the lesion, i.e., associate the lesion with a type. Some common types include fibroadenoma (FA), invasive ductal carcinoma plus DCIS component (IU), invasive ductal (ID) carcinoma, ductal carcinoma in-situ (DCIS), and invasive lobular (IL) carcinoma. Generally, a value of confidence level that a suspected lesion may be of a particular type is first computed. If the value of confidence level falls within a defied confidence range, the lesion is tagged as belonging to that type, FIG. 5 shows a suspected lesion being tagged as a DCIS type 502.

Figure 5:
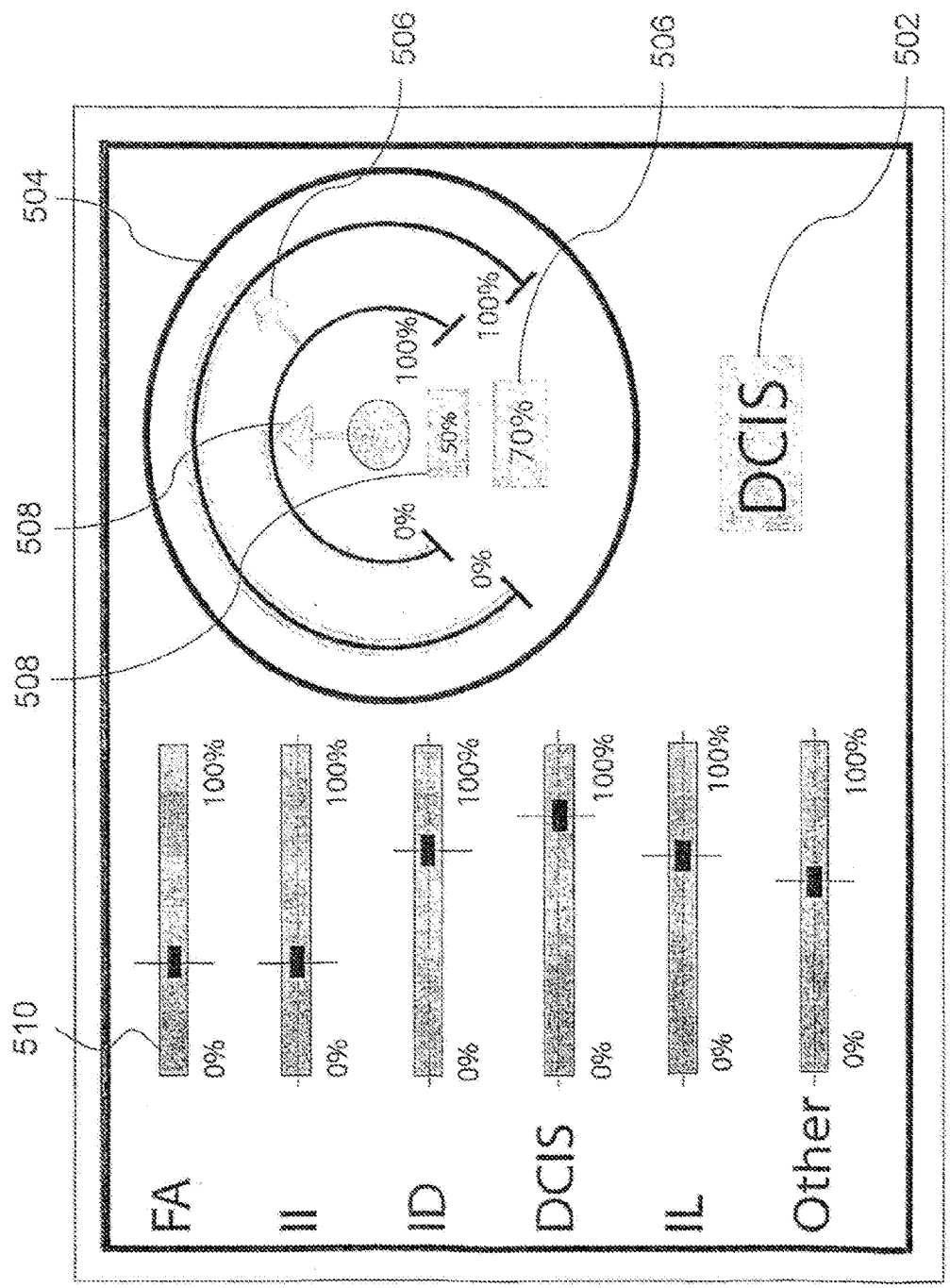
FIG. 5 shows a suspect lesion being tagged as a type DCIS lesion in an exemplary screen display generated by the system shown in FIG. 1.

Referring to FIG. 5, a controller 504, such as a knob-shaped activatable area on a graphic user interface, allows a user to set a confidence range defined by an upper threshold 506 and a lower threshold 508. FIG. 5 also can optionally display values of confidence level computed for different types on sliding rulers 510, to indicate the confidence level associated with lesion types. For example, FIG. 5 shows graphically values of confidence level for types FA, II, ID, IL together with tagged type DCIS. This advantageously provides feedback to the user as to a likely type of the suspect lesion. Although FIG. 5 shows only one type being associated with a lesion, it is possible that several types have the values of confidence level associated therewith falling within the confidence range. The system may then require a user to select a type, which may be a type with its value of confidence level failing within the defined range, or may be one outside the range. Alternatively, if a type has the largest value of confidence level, the system may also automatically tag the lesion to be of that type.

To supplement the automated detection of characteristics, an annotation tool, implemented as an annotation and modification module 212 is provided so that a user may add annotations to an image or modify annotations already entered. Here, annotation generally refers to association of regions of a medical image, features or characteristics of the regions or patterns in or adjacent a region with features selected from a pre-defined set of features, such as that defined by BI-RADS. With the aid of annotation and modification module 212, a user can also add features that are not identified by the software system 130 or remove false positives, i.e., features automatically detected by the system but are considered false detection. A user can also assign a different probability to a feature or modify a probability assigned by the system. Advantageously, as the list of features and their respective probabilities are modified by the user, the system automatically re-computes its automated assessment, to give the user an immediate feedback so the user can make a more accurate and improved diagnosis.

Figure 6:
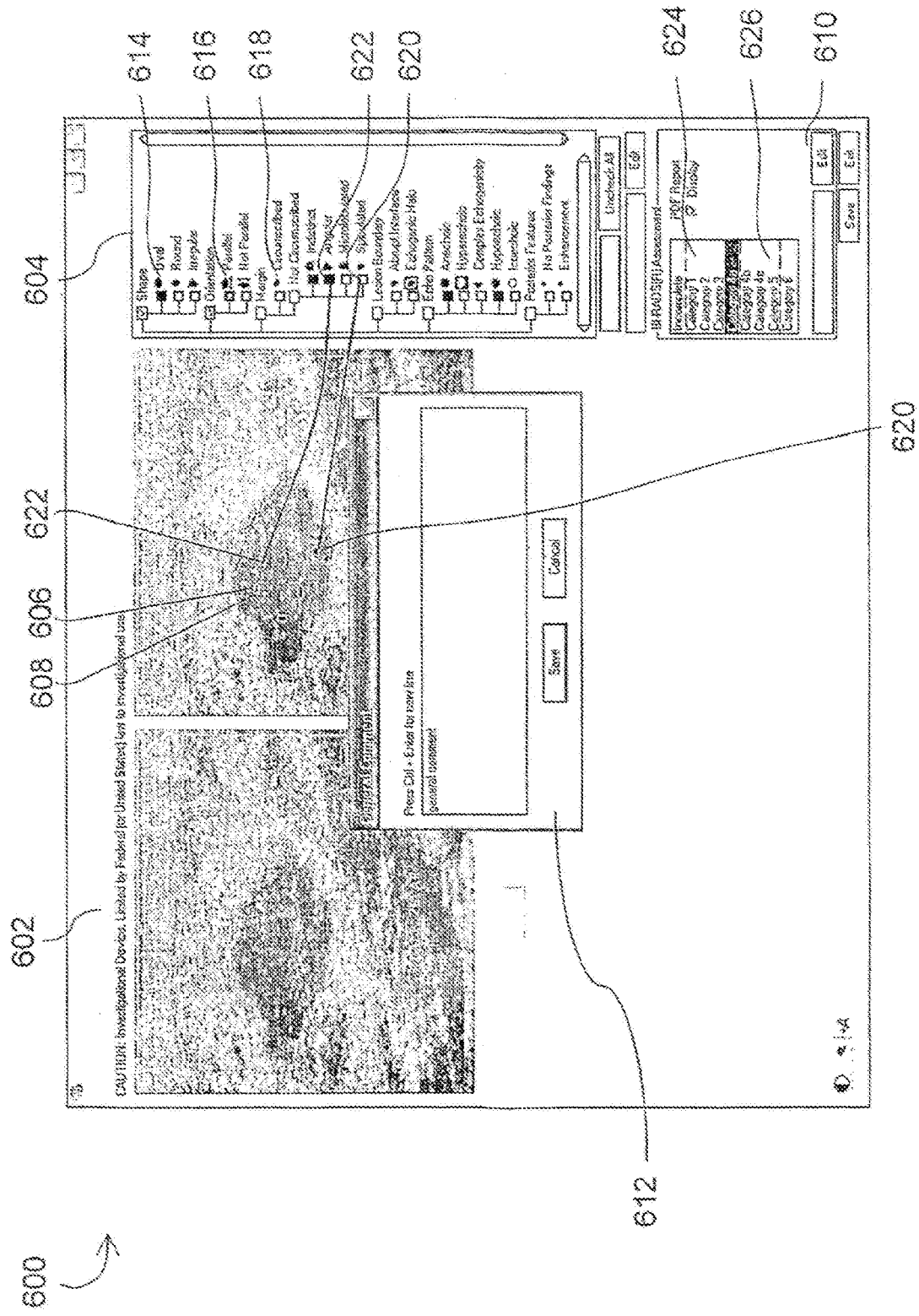
FIG. 6 shows an exemplary screen display presented to a user of the system shown in FIG. 1, that displays initial results for further evaluation by the user, the display being the result of processing of the segmentation candidate selected by the user from one of the segmentation candidates shown in FIG. 6.

The annotation and modification module 212 provides a list of detected characteristics for a user to review and annotate. Such a list may be presented to a user in a results window 600 as shown in FIG. 6. The results window 600 contains a complete list of a set of pre-defined characteristics, with the detected characteristics pre-populated. Any suitable set of pre-defined characteristics may be used, Some of them include Stavros characteristics and BI-RADS lexicon. In one implementation, the pre-defined set is that of BI-RADS. The results window 600 may be presented to a user on the display 114. It may also be made available to a web browser 122 connected to the system remotely. The results window 600 shown in FIG. 6 has an image window 602 and a results panel 604. A composite image is displayed in the image window 602 along with an original image. Features detected 606 are indicated in the composite image where possible. Some of the features are annotated. An icon, symbol or other graphical representation may be used to indicate an annotation 608. In the bottom portion of the results window 600 is a diagnosis panel 610 for displaying computed diagnosis and for the user to select a validated diagnosis. Also shown at the bottom of the results window 600 is a comment window 612 for entering comments and annotations.

Together with the composite image displayed in the image window 602, features detected automatically by the system are preferably presented to the user in the results panel 604 in a tree-structured feature list. Referring to FIG. 6, the results panel 604 shows a series of checkboxes 614 linked in a tree-structure to indicate their interrelationship. Each checkbox in FIG. 6 corresponds to a characteristic of the Stavros characteristics. Some of these checkboxes are activated, i.e., highlighted or checked. A checked checkbox 616 indicates that the feature has been detected in the image displayed in the image window 602 on the left hand side. An unchecked checkbox 618 indicates that the corresponding characteristic or feature is not detected in the image.

The user can modify the automated detection by removing a detected characteristic from the list or add a characteristic to the list. If the removed characteristic can be traced back to a region in the image, the displayed image may be automatically updated to indicate the removal of the characteristic, for example, by removing the corresponding icon. Conversely, a user can add a characteristic that has not been identified by the system in an automated detection process, namely, to identify a location in the medical image as the site of the characteristic. A characteristic manually added to an image can be automatically added to the list of identified characteristics. The annotation and modification module 212 allows the user to verify and confirm the system findings and make any necessary modifications based on his or her judgment and expertise. Annotations can be applied multiple times to each image. Referring to FIG. 6, if a user unchecks a characteristic that can be traced back to the image in the image window 602, the unchecked characteristic 620 is removed automatically from the image. To add a characteristic, the user may simply check the checkbox corresponding to the characteristic. The user may also use the annotation tool to drag a checkbox corresponding to the characteristic to be added to a desired location on the image and release it. A symbol or icon representative of the selected characteristic 622 will be dropped at the selected location. A user can then enter or edit a comment in the comment window 612 per added annotation. This step can be repeated for as many annotations and characteristics as desired or required. Each time a characteristic is added or removed, the image is updated where possible. In other words, if the characteristics may be represented by a symbol or icon image, that symbol or icon is also added or removed.

As the list of features (or characteristics) is modified or updated by the user, the system also updates its computed diagnosis at the same time. It will be appreciated that when a user adds a new feature, the user may also assign a probability to that finding. In one implementation, all user added features are assigned a probability of 100% and all user removed features are assigned a probability of 0%, but other values of a probability can be assigned, too.

In one implementation of the system, nine different diagnosis categories are provided, namely, {Incomplete, 1, 2, 3, 4a, 4b, 4c, 5 and 6}. This set corresponds to the categories used in BI-RADS. According to this scheme, 1 is Negative, 2 is Benign Finding, 3 is Probably Benign Finding, 4 is Suspicious Abnormality (which is further sub-divided or refined in the field by radiologists into 4a, 4b and 4c: 4a is finding with a low suspicion of being cancerous, 4b is finding with an intermediate suspicion of being cancerous and 4c finding of moderate concern of being cancerous, but not as high as Category 5), 5 is Highly Suggestive of Malignancy and 6 is Known Cancer.

These possible diagnosis are divided into groups, or buckets. Different granularity, i.e., different number of buckets, may be implemented. In one implementation, a two-bucket approach is taken. In the diagnosis panel 610, the first bucket 624 is shown to include diagnosis 1, 2 and 3 and the second bucket 626 includes diagnosis 4a, 4b, 4c and 5. In the initial results displayed, the system will only highlight one of the two groups instead of any particular diagnosis. A user may select a diagnosis from the group, making a diagnosis. The user may also override the system and select a diagnosis outside the group if the user strongly disagrees with an automated diagnosis computed by the system. As will be described later, a user may be required to select a diagnosis before the system will produce any report.

In one implementation, a user must validate a diagnosis by selecting one diagnosis from a default group, i.e., by selecting one diagnosis from either the first bucket 624 or the second bucket 626. Without selecting a diagnosis, all possible diagnosis in the default group are highlighted. This tends to reduce the risk of accidentally confirming a diagnosis without a detailed examination of the results of automated detection.

Using the annotation and modification module 212, a user can annotate both benign and malignant sonographic characteristics as described above. Annotation and modification module 212 also allows a user to add comments and notes related to annotations (annotation comment) or general notes related to the image (general comments). A general comment may be entered in the comment window 612. These comments and notes may be entered as text, picked from a list of pro-defined comments, or transcribed by a voice-to-text module.

Figure 7:
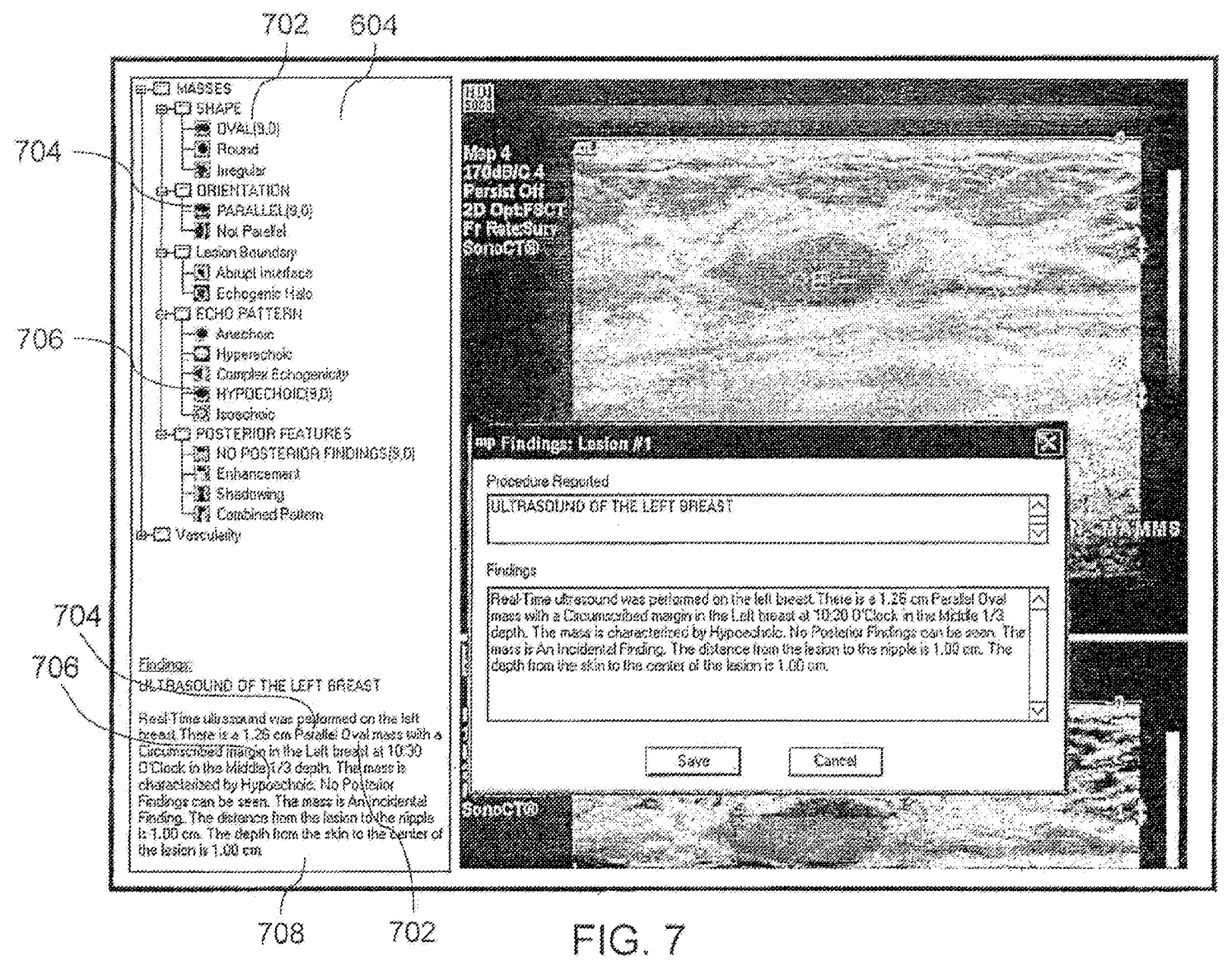

Conveniently, the annotation and modification module 212 may include an optional build-in template for generating a summary text, or summary note, as part of the general notes, reporting findings and the radiologist's assessment. The template provides the basic structure of a summary text, with suitable statements selectable by the annotation and modification module 212 based on findings and the validated assessment. The template may be modified by individual radiologists according to radiologists' style to provide more flexibility. Notes generated from a template can be further edited to provide more flexibility. FIG. 7 shows an exemplary screen display that a radiologist may use for saving a system generated summary text on findings as part of a general note. A summary text providing the radiologist's impression of the lesion may be generated and saved similarly. As can be seen from FIG. 7, information relating to the lesion is inserted into the summary text and corresponds to that shown in the results panel 604. For example, that the lesion has an oval shape 702, a parallel orientation 704, is characterized by hypoechoic echo pattern 706 etc. is shown in both the results panel 604 and the Findings panel 708.

The report module 214 interacts with and directs the operation of output peripherals 118 of the system as well as communicating with the data warehouse 128. The report module 214 also interacts with the user interface 112 for displaying the processed image or any report. Once an assessment is validated by a user, the report module 214 produces a report for the current active image. The report may be printed on a printer 120, or may be an electronic report suitable for sharing or archiving in the data warehouse 128. One example may be a PDF report. The PDF report may be displayed, printed or stored if desired. Another example may be a DICOM-structured report. When requested, the report module 214 saves to the system's data warehouse 128 all information on the image, annotations and symbols, related comments, lesion boundaries, BI-RADS assessments and selected characteristics, as a part of a DICOM-structured report for that processed image. The same information may also be sent to a DICOM-compliant device 126 for storing or sharing with other physicians or radiologists.

The report contents are generally by default based on the data available in the processed image as annotated by the user and also contains other pertinent information, such as institution or patient identification information and the patient's demographic information. In other words, data available in the results window 600 are generally reflected in the report. The report may include detected features such as sonographic characteristics along with any annotations and comments and user modifications. Original medical image and its processed counterpart can be included as well. The report can also include other information such as institution information, patient demographic information, an overview of; the software application and its algorithm settings. Finally, the report may contain the image findings and assessment of the radiologists, for example, in a format complying with the ACR-BIRADS Ultrasonic Lexicon Classification form.

The report can be provided as a form, with suitable boxes checked to indicate findings and an assessment. Conveniently, the report may include a summary list, listing all identified features. The report may also include a summary text, or supplemented with a summary text. The summary text may be based on findings and impressions generated by the annotation and modification module 212 and further modified by a radiologist. The summary text may also include a recommendation whether biopsy should be performed.

A report may include identification information for traceability and auditing purposes. Identification information may include patient identification number, study identification number, unique report identifier, series number, time stamp, namely the time and date of the study or report, or other suitable identification information. Conveniently, a cryptographic module may be provided for signing the report digitally. An electronic signature generated by the cryptographic module may include some or all identification information to provide improved audit capability and to discourage accidental modification of the reports.

Multiple lesions from one image may be processed in one session, in which case, a single report containing all findings can be produced. Alternatively, multiple images may be processed in one session that leads to a single report containing all findings about all lesions in all images. The report can group the findings by lesion, characteristics identified, images processed or in some other fashion. An overall assessment, such as a BI-RAD assessment taking into account of findings about multiple lesions in a medical image, a single lesion seen in multiple images for the lesion, or multiple lesions in multiple related images, may also be provided.

Preferably, reports are archived as DICOM Secondary Capture. Annotations, comments, image processing results such as lesion boundaries and diagnosis results are archived as part of a DICOM-compliant file. A user can also save, for example, a PDF version of the report locally in a patient's instantiated directory. This facilitates easy future reference. If an instance for that composite rendering already exists in the archive for the; patient, a new instance is created. Audit information, such as user ID, date or time stamp, and user addition or modification of detected features, can be recorded for each archived instance.

Figure 8A:
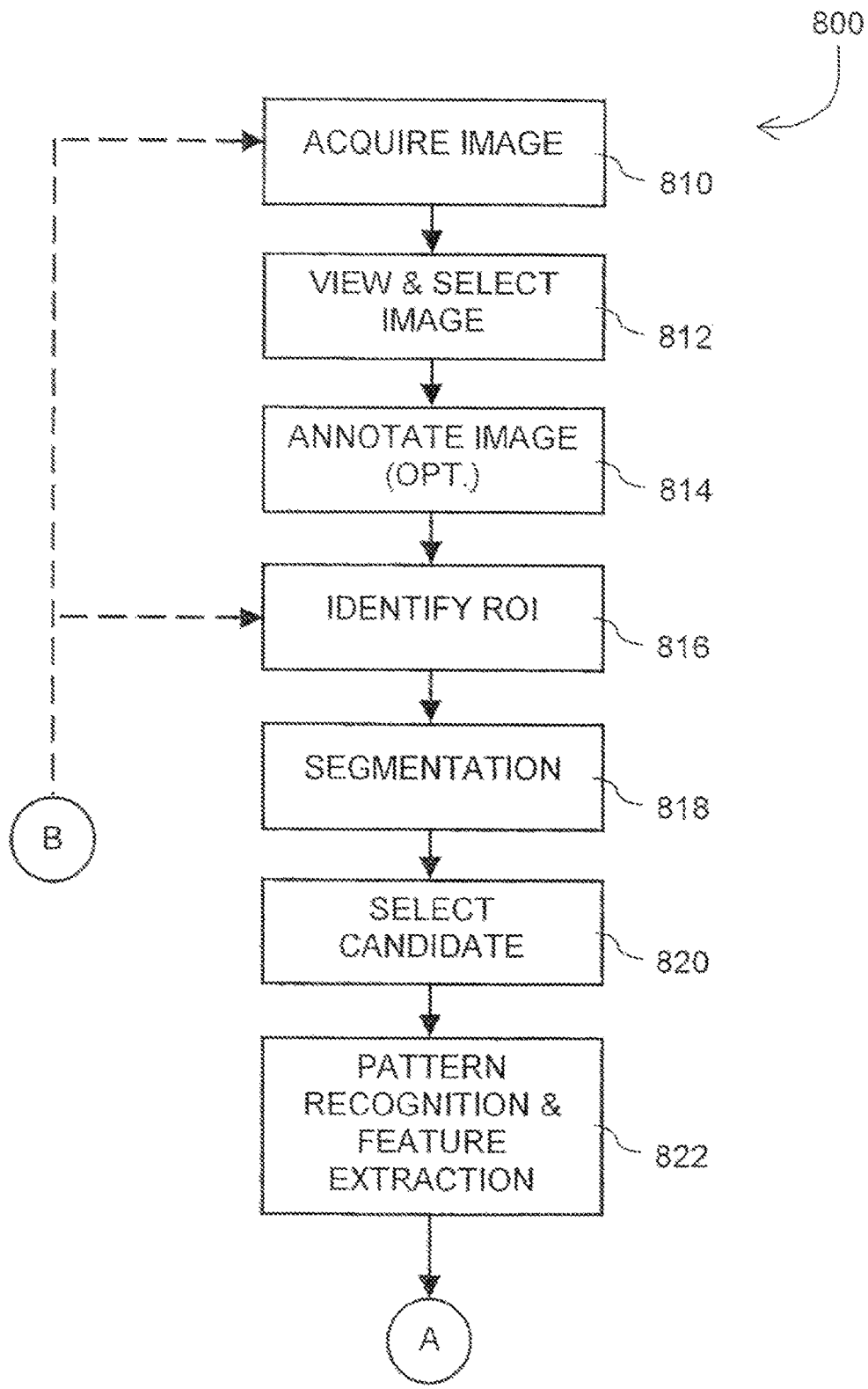
Figure 8B:
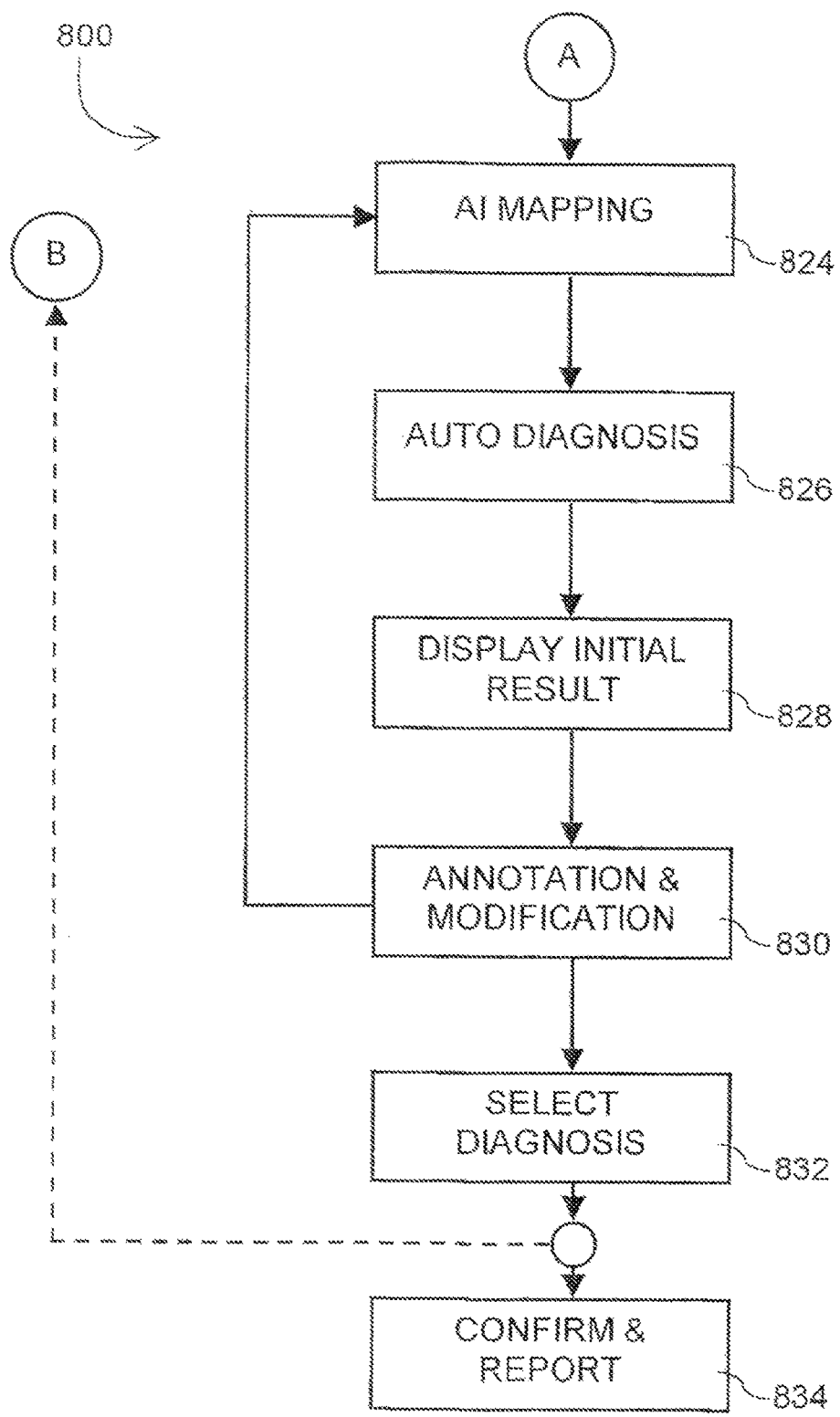

With reference to FIG. 8, steps of a workflow 800 are now described in detail. This is a work flow implemented by the system to match that of a radiologist but with further flexibility and user control built into the process. Images are first acquired and loaded by the image acquisition subsystem 102 under the control of image loader 204 at the image acquisition step 810. As described before, image loader 204 may load an image from a medical scanning device, load a medical image from the image database 110, or receive a medical image from a remote image server 108, among others.

Once the image is loaded, the image display and manipulation module 206 displays the image on the display 114 at step 812. The user can manipulate the presentation of the image in a variety of ways in order to better view the image either as a whole or focus on a particular region. For example, a user can zoom or pan the image. The user can adjust brightness and contrast levels of the image as displayed on the display 114. Thus, a user can examine the image in great detail as well as to view any suspicious regions in context. In one implementation, the image acquisition subsystem 102 supports the acquisition of multiple images. Image display and manipulation module 206 provides a predetermined number (for example, 4) of images for selection at step 812. For example, the image scanning device may provide several images of cross-sections of an anatomical part of a patient, such as a breast, for viewing and selection by the radiologist. The image display and manipulation module 206 may display all cross-section images on a display 114, or it may display only one of them, while displaying the rest as some thumbnail views. The user, such as a radiologist, may select one of the views for further evaluation and study. In case of breast ultrasound images, two views may be provided per case at the same time (one Radial and one Anti-Radial), also known as "R and AR views".

At a next step 814, the user may add annotations to the selected image as described in connection with the annotation and modification module 212. The user may also add annotations later after a results window 600 is pre-populated with automatically detected features. Next, the user initiates CAD processing by identifying and selecting an ROI at step 816. Once the ROI is identified at step 816, the segmentation module. 216 begins processing the image and attempts to identify possible boundaries of an abnormal region such as a nodule.

During a segmentation step 818, a series of possible boundaries, or contours of a suspected nodule, are generated. Instead of selecting one boundary automatically, the segmentation module 216 requests the image display and manipulation module 206 to overlay the possible boundaries with individual images to provide a series of candidate images and provide these candidate images for user selection.

Figure 4B:
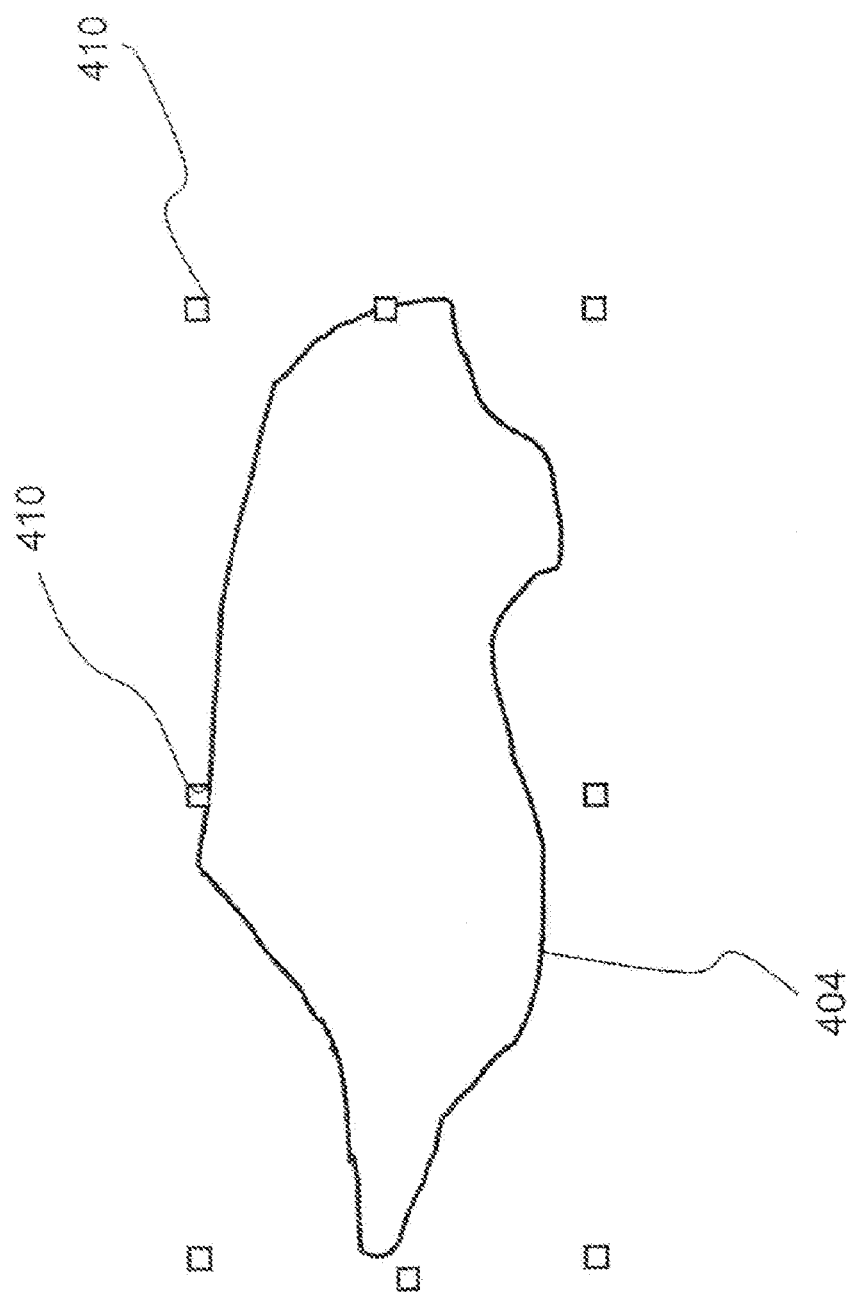
FIG. 4B illustrates schematically a segmentation candidate of FIG. 4A showing only its segmentation boundary outline and its control points.

At step 820, a user selects one of the candidates and communicates that selection to the system, for example, by pressing an "OK" button Once the system receives the selection from the user at step 818, the system starts further processing at step 822. At step 822, pattern recognition and feature extraction takes place. Optionally, a user may manually modify the selected contour by means of defining or modifying control points 410 on the candidate contour and moving or editing them as shown in FIG. 4B.

Features detected at step 822 are next provided to the decision module 210 for computing a computed diagnosis. The auto-diagnosis step may include an AI rule mapping 824 step, during which the AI rule module 222 maps these characteristics to an intermediate result based on a set of pre-defined AI rules. The assessment module 224 combines the result of AI rule mapping with the analysis of detected characteristics to arrive at an automated diagnosis at step 826.

At step 828, in a results window 600, the user is presented with an initial result from the automated detection process. The results window 600 is pre-populated with all detected features as well as with a group of suggested diagnosis.

A user can add or delete features by selecting or unselecting checkboxes shown in the results panel 604 (step 830). Based on this dynamically modified feature list as well as their assigned probabilities, auto assessment module 224 dynamically updates the computed diagnosis. A different group of diagnosis may be dynamically displayed if the modification of the feature list is such that the automated diagnosis changes from one group to the other, such as from one of 4a, 4b and 5 to one of 1, 2 or 3, or vice versa, Once a user is satisfied that features seen in the image are all selected in the feature panel and the checkboxes in the feature channel do not have any false detection, the user may confirm or select a diagnosis (step 832). After a diagnosis is validated or selected by the user, the reporting module 214 at step 834 automatically produces a report. Results from the analysis can be saved to a data warehouse 128, or shared with other physicians or radiologists. Audit trail of operations by the user, including selection of ROI, selection of segmentation candidates, annotation and modification of results and validation of diagnosis, can all be saved. This completes the image processing workflow 800.

As will be appreciated, although the workflow 800 described here is for processing one image at a time, with modification, the system may be used to process multiple lesions or multiple related images in one single session. For example, the system may be configured to permit the user to return to step 816 to select another lesion or ROI at the conclusion of step 832, instead or proceeding to the reporting step 834 directly. The user may also return to step 810 to load another image for processing in the same session. The system may also be further configured to correlate the same lesion shown in different images, After all lesions in the same image or all images are processed, the user can then proceed to step 834 to produce a single report, containing results on all lesions in all images processed. Further, a global assessment based on all characteristics identified in all lesions (in all images) may also be produced and presented to the user for review and validation.

Figure 9:
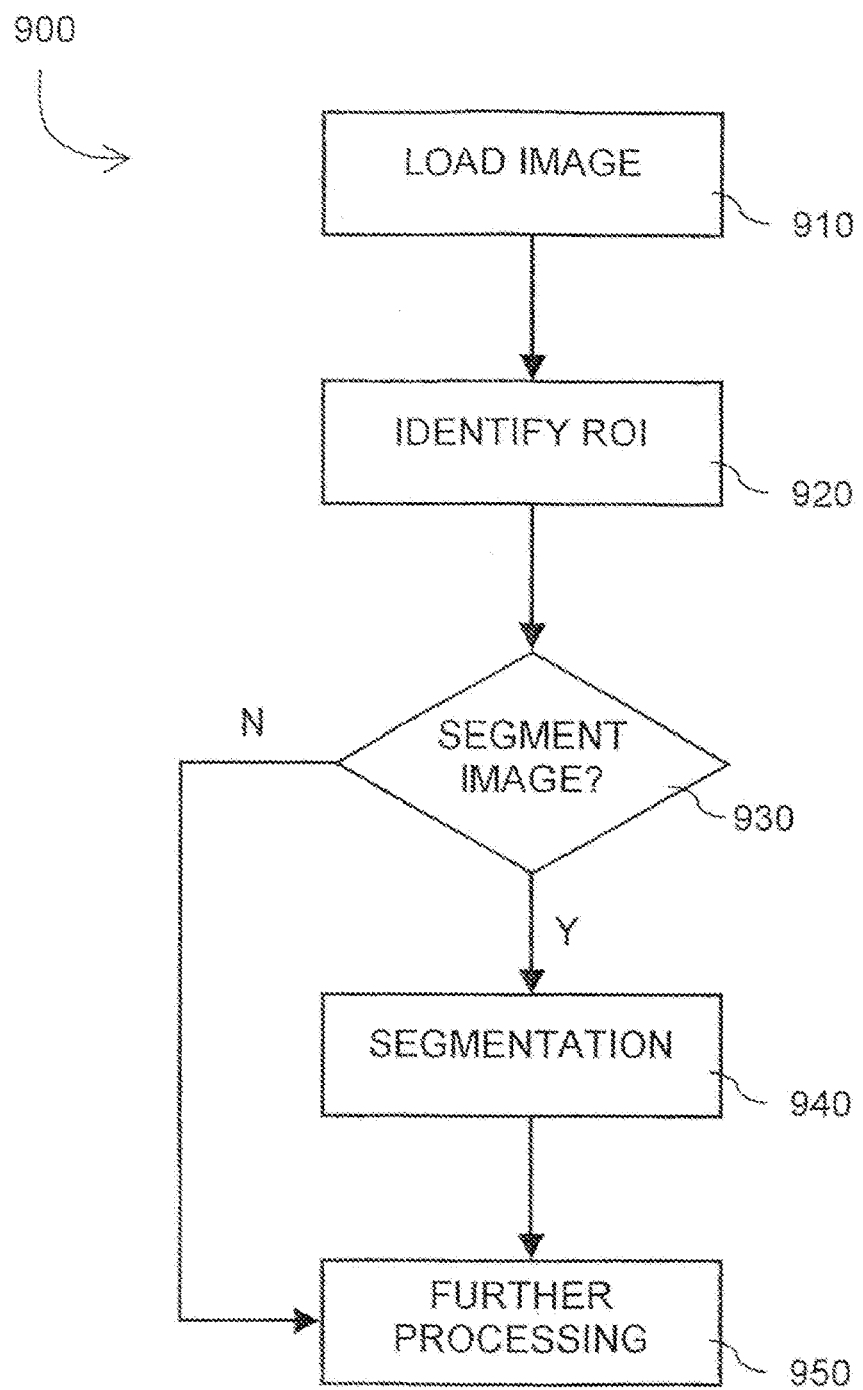
FIG. 9 shows a process modified from that shown in FIGS. 8A and 8B for processing multiple images for a single lesion in a loop.

In one implementation, the system is configured to assist a user to process multiple images for a single lesion, Referring to FIG. 9, there is shown a process for processing multiple images for a single lesion in a loop 900. At step 910, one of the multiple images is first loaded. The loaded image may be segmented already, or not segmented as yet. Once loaded, an ROI is identified at step 920, for example by identifying its "seed point" and size using a graphical pointing device as shown in FIG. 3A or through identification parameters entered in a window as that shown in FIG. 3B. Next, the image is examined at step 930 to determine whether the identified ROI is segmented. If it is already segmented, then segmentation 940 may be bypassed. A user may also elect to bypass segmentation even if an image is not segmented. As described earlier, a user may use the annotation tool to identify a list of features to the system, from which the system also can compute a diagnosis. If segmentation is to be bypassed, the system proceeds to step 950 for further processing, such as pattern recognition, feature extraction and diagnosis computation. Alternatively, or if the ROI is to be segmented, the image is forwarded to segmentation module 216 for segmentation 940 and further processing.

After the image is processed, for example, following the remaining steps 818 to 822 as described in reference to FIG. 8, the process may return to the beginning of the loop 900 and loads a second image. At the identification step 920, the ROI is again identified. At the next step, the ROI is examined to determine if it is already segmented or segmentation is required. Conveniently, the segmented lesion in the second image can be correlated to the lesion in the first image if the second image is segmented; or, the location and boundary of the lesion segmented in the first image can be advantageously used as first inputs for segmenting the lesion in the second image. The second image is then processed and the process returns to the beginning of the loop 900 until each of the multiple images is processed.

Figure 10:
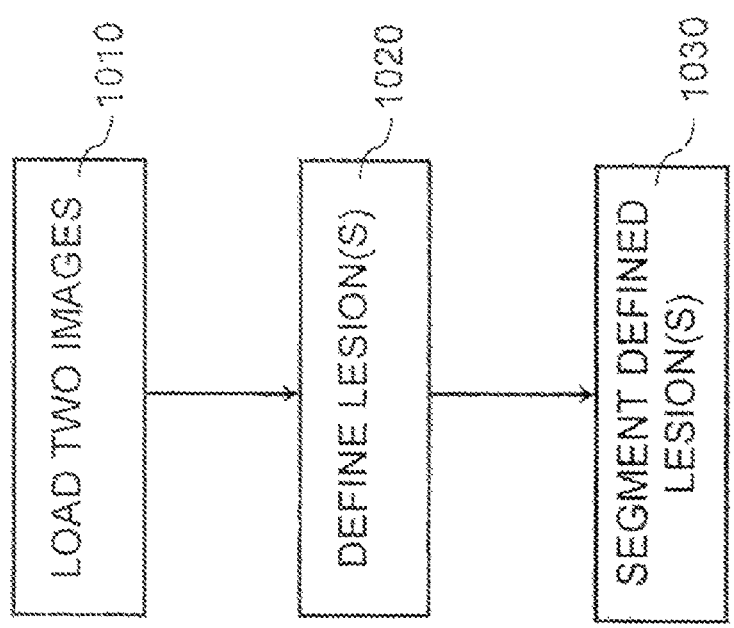
FIG. 10 shows steps of another process modified from that shown in FIGS. 8A and 8B for segmenting multiple lesions per image, or several lesions on multiple images.

In another implementation, the system is configured to assist a user to process multiple lesions per image, or several lesions on multiple images. FIG. 10 shows a series of steps followed by a user for segmenting two lesions per image, and two images for these two lesions. FIGS. 11A to 11D are some exemplary screens produced by the system as a user follows the steps shown in FIG. 10.

Figure 11A:
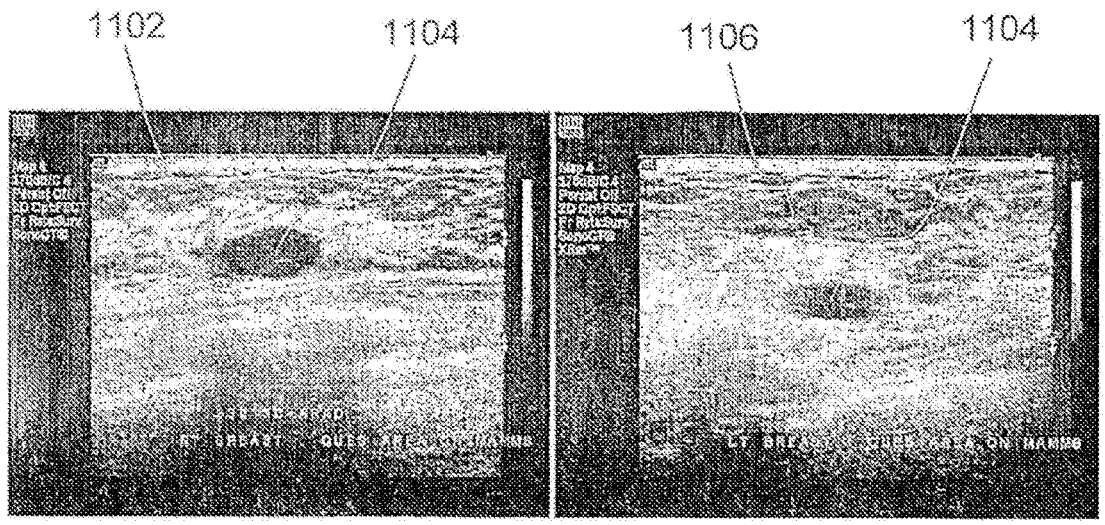
FIGS. 11A to 11D are some exemplary screen displays produced by the system as a user follows the steps shown in FIG. 10.

At step 1010, two images are loaded and shown to a user for selection of lesion candidates, FIG. 11A shows a first image 1102 containing a first lesion 1104 and a second image 1106 also containing the first lesion 1104, as displayed to the user. At step 1020, the user enters parameters for defining the first lesion 1104. One example of defining a lesion is described earlier i reference to FIG. 3B. At step 1020, a second lesion 1108 is also similarly defined.

Figure 11B:
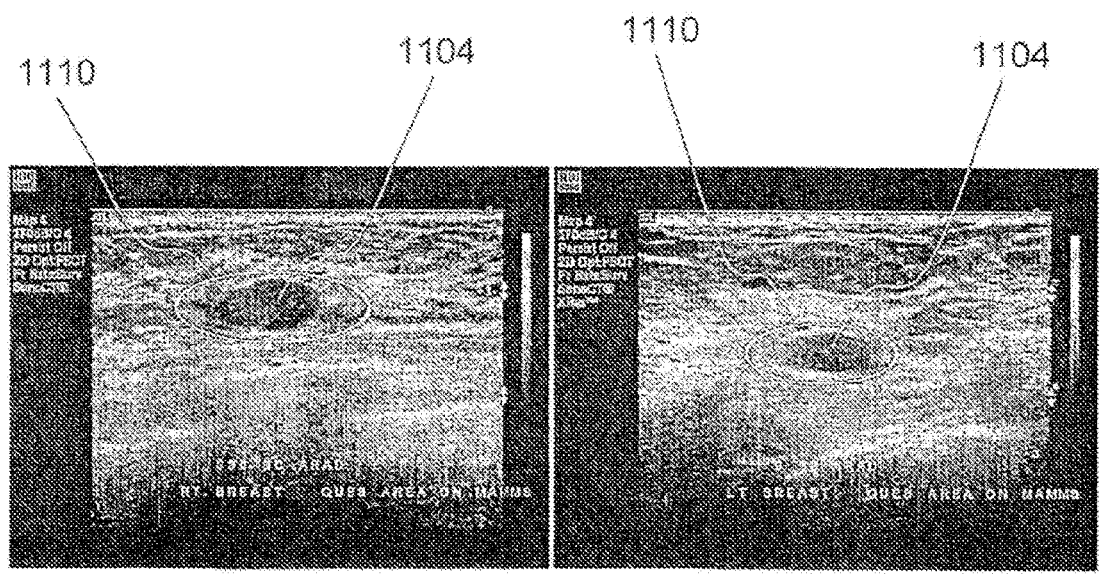

A lesion so identified may be marked with a circle or a generally oval curve encircling the lesion, on a composite image including the image and the marking circle or oval curve. FIG. 11B shows the first lesion 1104 marked with an oval curve 1110, on both the first image 1102 and the second image 1106.

Figure 11C:
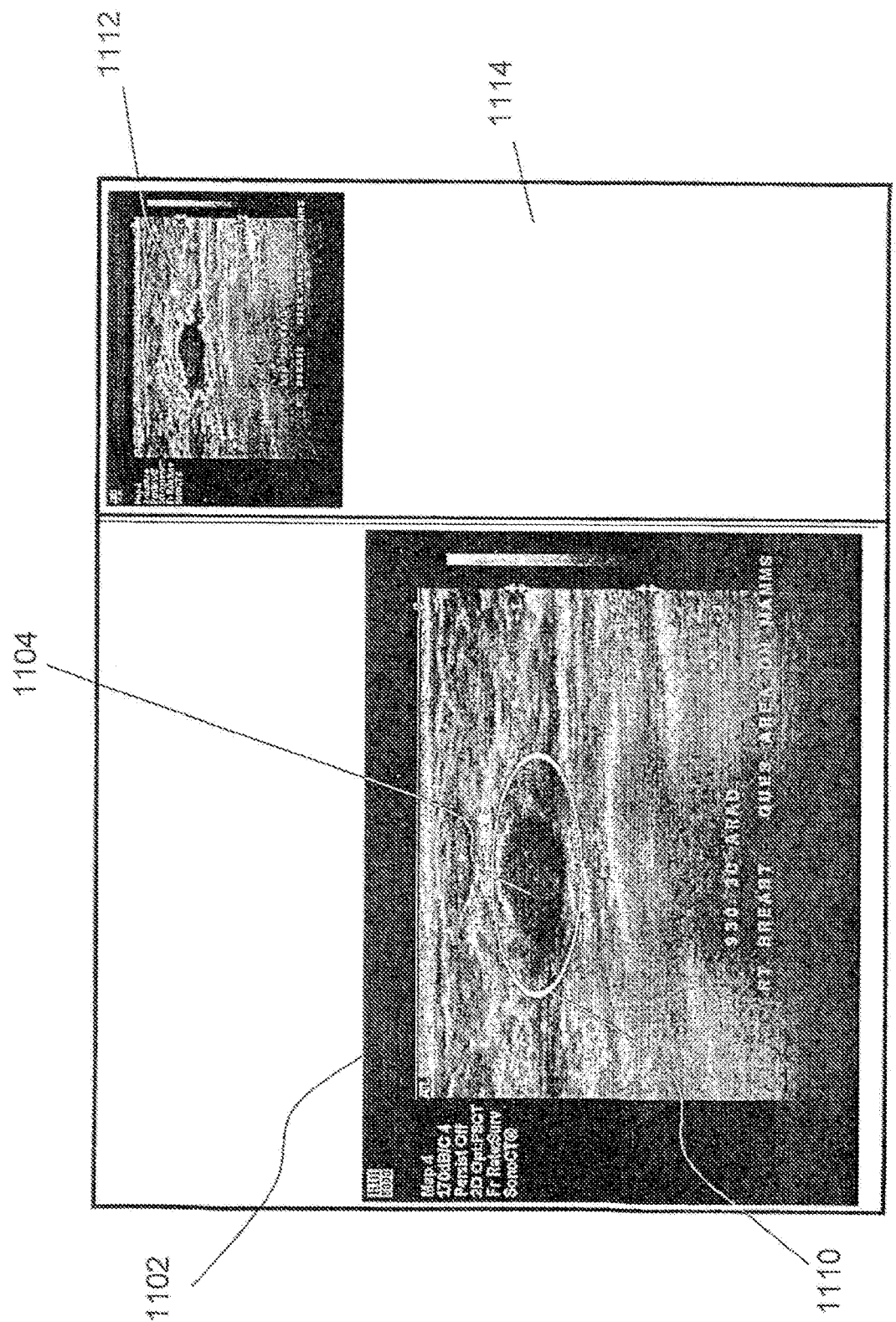
Figure 11D:
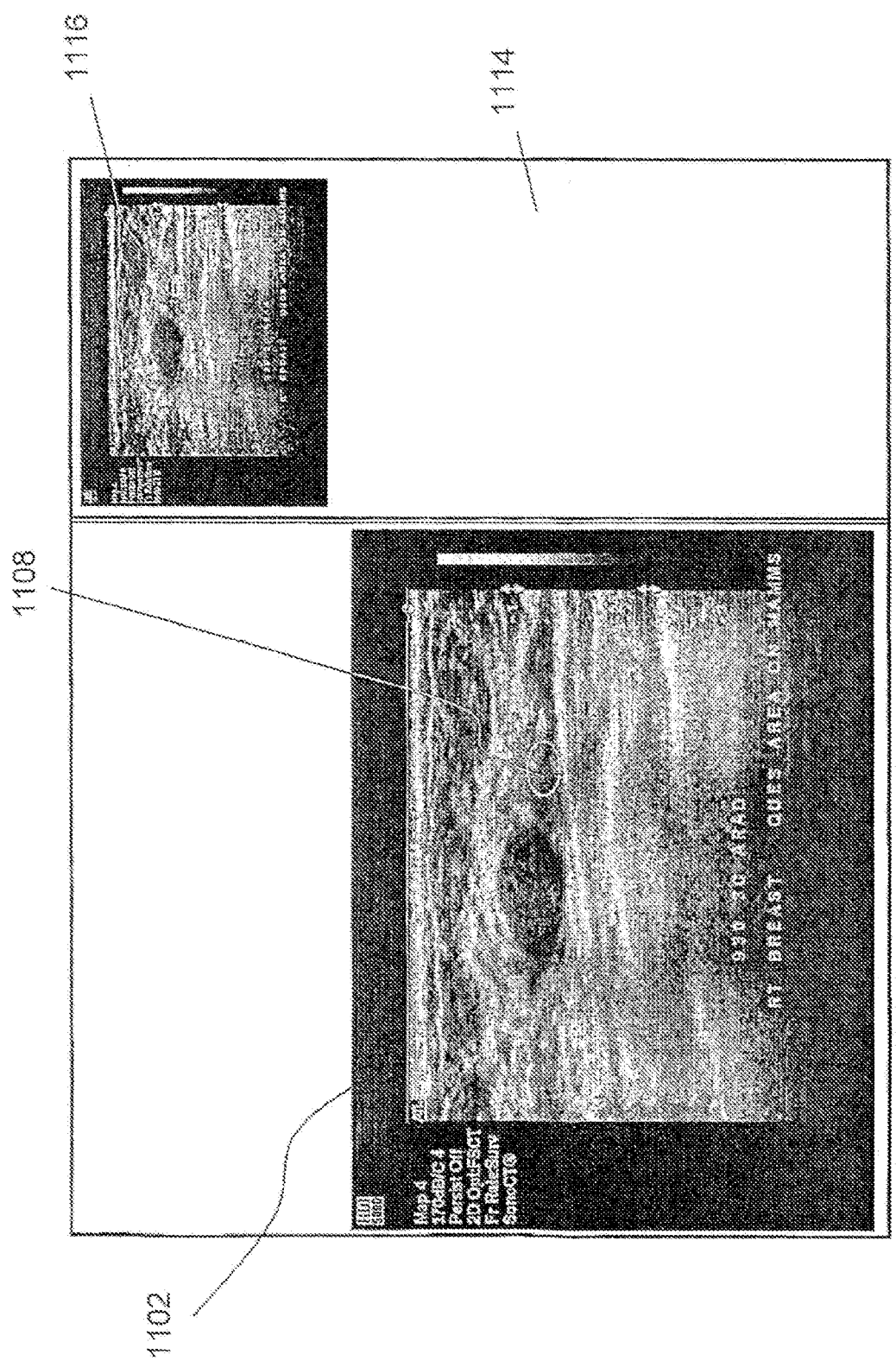

Referring back to FIG. 10, a lesion identified at step 1020 is segmented. The system may segment the image as described before, providing several segmentation candidates for selection. The image with an ROI identified and the image now segmented and selected by the user may be displayed side by side, As an example, FIG. 11C shows a single segmentation candidate 1112 in a segmentation panel 1114 on the right hand side and an oval curve 1110 encircling the first lesion 1104 in the first image 1102 on the left hand side. In this example, only one segmentation candidate is provided by the system although it will be understood that multiple candidates are provided in general. FIG. 11D shows a segmentation candidate 1116 in a segmentation panel 1114 and the second lesion 1108 in the first image 1102 on the left hand side.

In another implementation, the system may take advantage of its ability of loading several images for a single lesion to perform segmentation in a three-dimensional space. As will be appreciated, a three-dimensional region can be represented by a series of slices. Each slice may be a two-dimensional image and contains a region corresponding to the lesion. As the series of images, or slices, are loaded, the representation of the lesion in each slice can be correlated with each other. The stack of slices thus provides a three-dimensional data set. As in a 2-dimensional segmentation process, the system can also segment the three-dimensional dataset and provides series of segmentation candidates in the three-dimension space for user selection, each segmentation candidate being a three-dimensional envelop enclosing the suspect lesion. A user can select one envelop from the candidates that best fits the boundary of the suspect lesion.

In a further modified implementation, the CAD system displays in a temporary window, i.e., a temporarily allocated display region, a series of images for user review and selection. Advantageously, these images displayed in the temporary window can be "thumbnail" images. For example, at step 910, instead of loading one image, several thumbnail images may be loaded in the temporary window for selection. A thumbnail image is a version of a loaded medical image, generally with a reduced size, for example, by reducing its resolution. Because of its reduced size, a thumbnail image generally permits faster processing and manipulation. Images corresponding to these thumbnail images can be different slices of a three-dimensional data set, can be different versions of a medical image having different lesions highlighted, can be different medical images showing the same lesion, or images of the same region taken at different times, or a combination thereof, among others. These images can be images acquired in real-time or images retrieved from archives.

These thumbnail images can be a series of images with suspect lesion candidates highlighted for user review and selection. Conveniently, these lesion candidates can be automatically identified by the system. For example, the system may image processor may be provided with a lesion locator for this purpose. The lesion locator first scans all pixels in each of the images corresponding to the thumbnail images and performs an image analysis. Regions that appear to have distinct features may be suggested as regions corresponding to lesion candidates to a user. Alternatively, regions having characteristics like texture that differs from the background may be suggested as lesion candidates to a user. Thus, the system can dynamically provide a number of lesion candidates for user selection, without requiring the user to identify, or define a region of interest to the system first. The system may further segment each of the regions corresponding to lesion candidates and present to the user, along with each lesion candidate, the best segmentation candidate for each lesion candidate. Thus, the steps 920 to 940 may be automated, with minimum user intervention. This provides further assistance to a user in identifying lesions in medical images.

It will be appreciated that lesion candidates can be identified using any suitable method, not restricted to examples described above. For example, in the case of a three-dimensional data set, lesions identified in one of the slices can provide indication of lesions in neighboring slices. As another example, an MRI data set may be a series of contrast-enhanced MRI images obtained at regular time intervals. Before or during the exam, a contrast enhancement agent is injected into a vein in a patient's arm. Typically, a gadolinium based contrast agent (e.g., Gd-DTPA) is used. The use of contrast agents tends to provide greater contrast between normal and abnormal tissues. Analyzing the time-variation of enhancement also facilitate delineating a sub-set, or sub-volume, of imaged region, or multiple sub-sets, as lesion candidates, which the system can suggest to a user.

Advantageously, the temporary window for displaying thumbnail images can be configured for displaying thumbnail images that may be of interest to a user. For example, a user may select an image and place it in the temporary window for later processing. The image placed there may have been processed, partially processed, or not processed at all. A partially processed image may have a few lesions identified by the user but have not been processed to extract features from the lesions. Conveniently, the CAD system may process all newly acquired images to identify lesion candidates as described above and place in the temporary window those images that contain at least one suspect lesion. Thus, the temporary window may have placed therein a series of thumbnail images corresponding to images that a user may wish to examine further. Preferably, the thumbnail images are ranked to assist a radiologist to prioritize them. Any suitable ranking system may be used. For example, the list of thumbnail images can be ranked by the likelihood that an image contains a lesion. The image with the most suspicious lesion is then placed on the top of the list. Or, a coloring system can be developed to indicate the likelihood. For example, a red outline can be used to indicate that a lesion candidate is most suspicious, yellow for significant suspicion, and blue for unprocessed images. Different ranking system may also be combined to provide better assistance to a radiologist.

Once a candidate lesion is identified, either selected by the user or by the system, the user may continue with the CAD process. For example, the CAD process may continue with extracting features associated with the candidate lesion and computing a diagnosis from the extracted features, the details of which have been described earlier. Of course, the user may also elect to bypass pattern recognition and feature extraction and decide to select manually features within the medical images, as described earlier. The CAD software 130 is then used for computing a diagnosis from manually identified features associated with the lesion or lesions.

In operation, a user first initiates the CAD process by acquiring an image or several images so that the system 100 may load the image or images for review and further analysis. Such further review may be based on a user-identified ROI or a general evaluation. The system or software system initially displays a gallery of several for example 6, candidates of segmented images or candidates of suspect lesions on the display 114. The user may select any candidate and perform the interactive, controlled image analysis in real-time for further analysis of anatomy and pathology, If the images are acquired in real-time, the system may be configured to provide feedback to the user and guide the user to adjust the medical scanning device 104 to acquire a better image. This enables a radiologist to obtain an optimal image during one examination session, without having to recall a patient for another examination due to, suboptimal images being obtained. Suboptimal images may be caused by, for example, artificial shadowing due to improper orientation or positioning of an ultrasonic transducer. With real-time feedback, the user may adjust the orientation or position of the ultrasonic transducer to remove any artificial shadowing. Or, the user may move the transducer to sweep across a suspected region. A frame-grabbing technology can be implemented to help identify the best orientation or position of the instrument. As inappropriate pressure applied at the interface of transducer/gel/skin may degrade the quality of ultrasound images obtained, the system can provide feedback in real-time, for example, via audible alert, if too much pressure is applied.

With the aid of a CAD system, a user can therefore obtain an optimal image or images for more clearly showing any abnormalities that may present in the tissue. The following steps can be followed. The image is first segmented if desirable, with a number of segmentation candidates presented for selection. The system processes the selected segmentation candidate and identifies, or extracts, features that are considered relevant to a diagnosis. An automated diagnosis is made based on the features extracted and identified. The system displays a composite rendering of the input image with detected characteristics superimposed. The composite rendering by default displays all of the detected characteristics. The detected characteristics are pre-populated automatically in the results window 600 as, a list of detected characteristics.

Further user control of the detection process is possible at this point. For example; as described before, a user may add or remove any or all characteristics originally identified by the system. The AI rule module 222 and the assessment module 224 automatically computes or re-computes a diagnosis based on the modification by the user and then updates a BI-RADS assessment automatically. A report can be generated upon a diagnosis being validated by a user. Alternatively, the user may move or adjust the medical scanning device in order to obtain a better image, from which features are identified or extracted with a higher confidence level. The user can keep adjusting the medical scanning device and reviewing the results of image processing and analysis until an optimal image is obtained.

Figure 12:
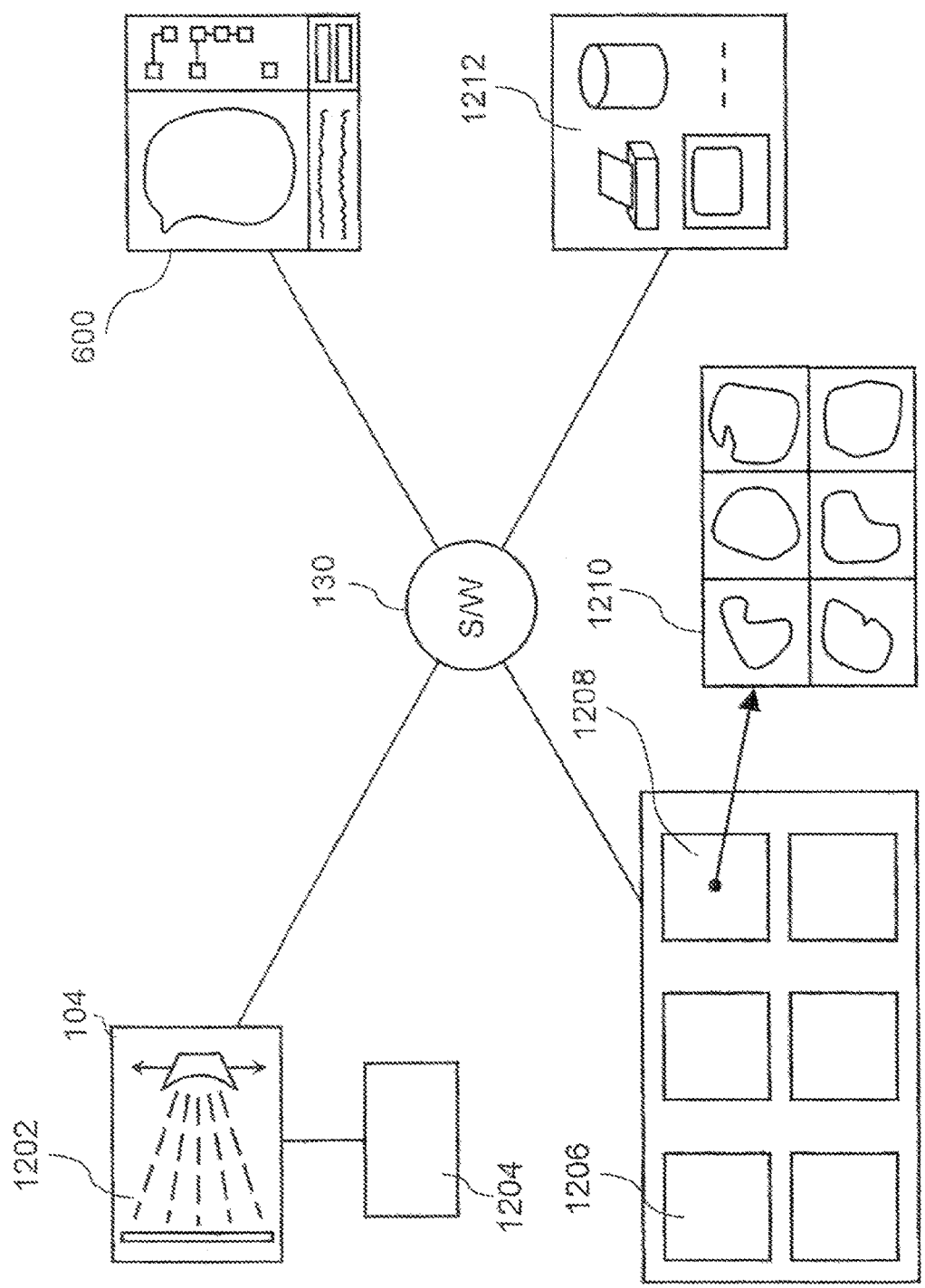
FIG. 12 shows schematically a CAD system implemented differently from that shown in FIG. 1.

As described earlier, different medical imaging devices may be integrated with a CAD system. In one implementation as shown in FIG. 12, the medical scanning device 104 is an ultrasound machine 1202 that has a dedicated software application 1204 for indexing image frames with positioning and orientation of ultrasound transducer. The software application 1204 is operatively connected to both the ultrasound machine 1202 and the CAD software system 130. Any medical images acquired by the ultrasound machine 1202 has an index, which corresponds to a position coordinate and orientation angle of the transducer when taking the image. As an operator of the ultrasound machine 1202 moves the transducer of the ultrasound machine 1202 around a patient, a series of images 1206 are produced, each having a location and an orientation index. The operator may review the series of images, and select one that is considered of the best quality from the series of images for fit processing. For example, once selected, the best image 1208 may be segmented and a gallery of six segmentation candidates may be displayed in a temporary window 1210 for user selection and that further feature extraction can be performed on the selected segmentation candidate. Alternatively, the operator may feed the series of images to the CAD software system 130 to initiate a CAD process on each of the acquired images.

As described earlier, the CAD software system 130 can be used to identify and extract a list of features from each of the images and compute an automated diagnosis based on the features extracted and identified. It may be possible that the operator may decide, before the CAD process is completed for all of the images, that the series of images do not represent optimal imaging. For example, it may be possible that because of improper positioning or orientation of the transducer, some artificial shadowing is introduced into the images. The artificial shadowing may cause difficulties for the CAD software system 130 to correctly identify true abnormalities in the images. Inappropriate pressure applied to an ultrasound transducer may also degrade the image quality. The early discovery of poor quality of the images allows an operator to adjust detection parameters such as position, orientation or pressure of the transducer, or even the position of the patient in order to get optimal images. This provides immediate feedback to the operator as to the quality of images obtained so that corrective actins, such as transducer repositioning, may be taken.

Once the operator is satisfied that the optimal images are obtained, the operator may select one best image 1208, so that the CAD software system 130 may continue with the CAD process, as described before. A list of automatically detected features as well as an automated diagnosis may be computed from the features once a segmentation candidate is selected by the user. The results are displayed in a results window 600. The user, as described before, may then confirm or modify the features automatically identified by the system, and then validate a diagnosis based on the suggested group of diagnosis presented to the user. The validated diagnosis, together with the medical images and other detection results, may be saved, transmitted for sharing with other radiologists, or used for producing a report, using the output devices 1212.

Figure 13A:
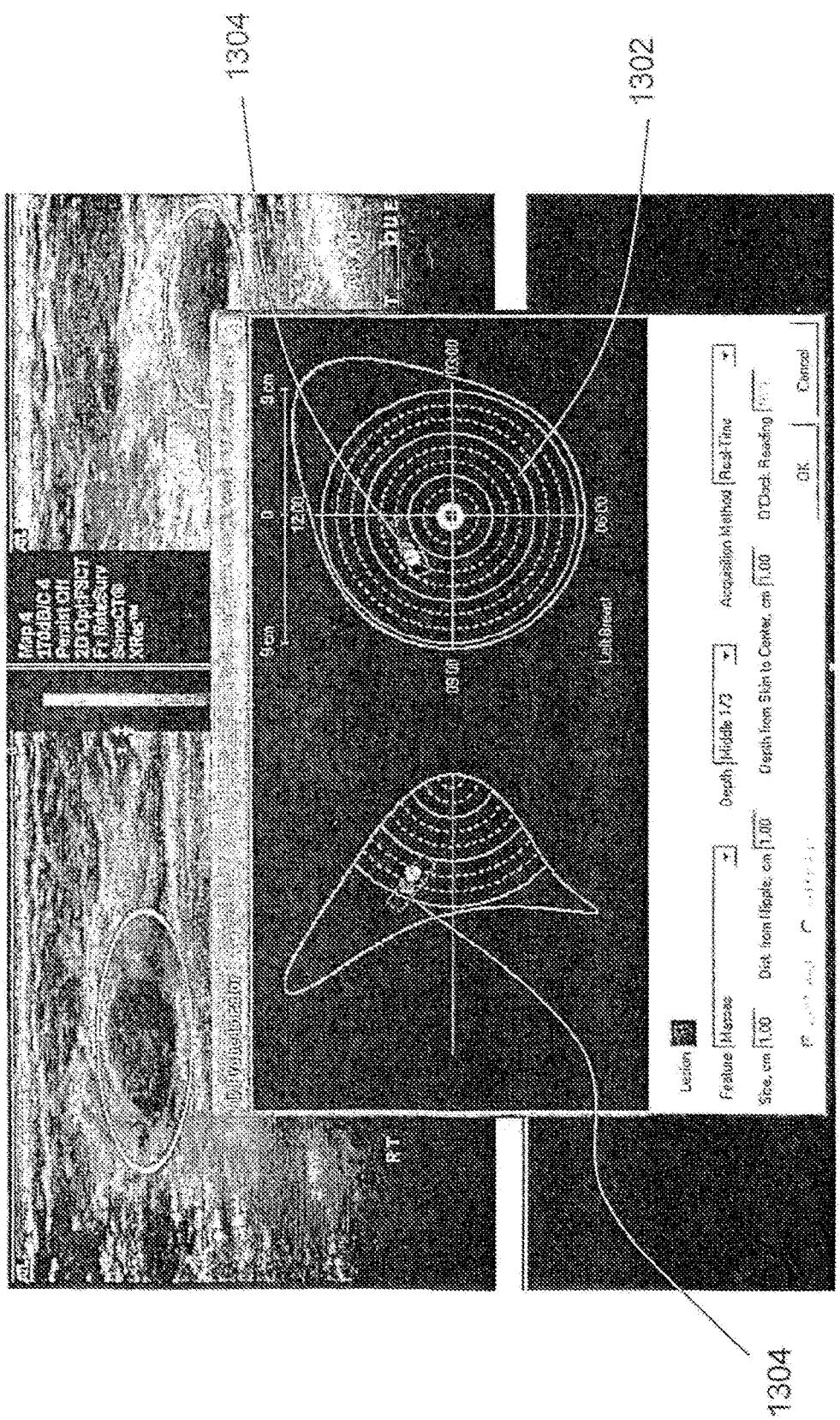
FIGS. 13A and 13B show an exemplary screen display that a user of the system shown in FIG. 12 may use to enter location and orientation information of a probe or transducer and a report incorporating such location and orientation information.
Figure 13B:
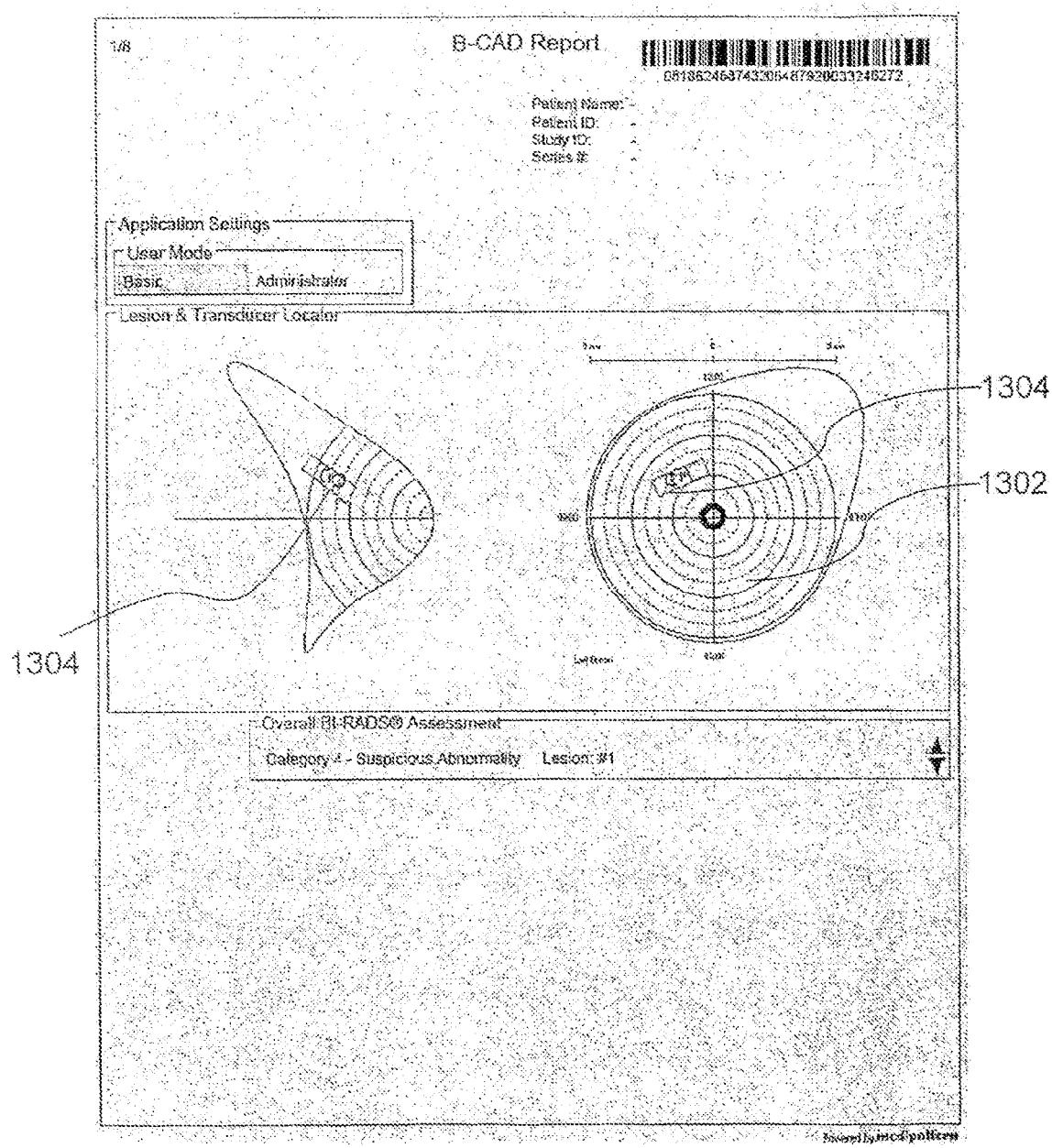

Advantageously, when the CAD software system 130 is connected to a transducer for obtaining images in real-time an operator may also enter the location and orientation of the transducer or probe through a probe/transducer location window for inclusion in a report FIG. 13A shows a graphical user interface for a user to enter the location and orientation information. The location may be entered by selecting a point in the wireframe diagram 1302. To facilitate entering orientation information, a rectangle 1304 for representing a probe or transducer is displaced superimposed onto the wireframe diagram. By rotating the rectangle 1304, an orientation of the probe or transducer may be entered. FIG. 13A to 13B shows a page of the report that provides the recorded location and orientation information.

Figure 14:
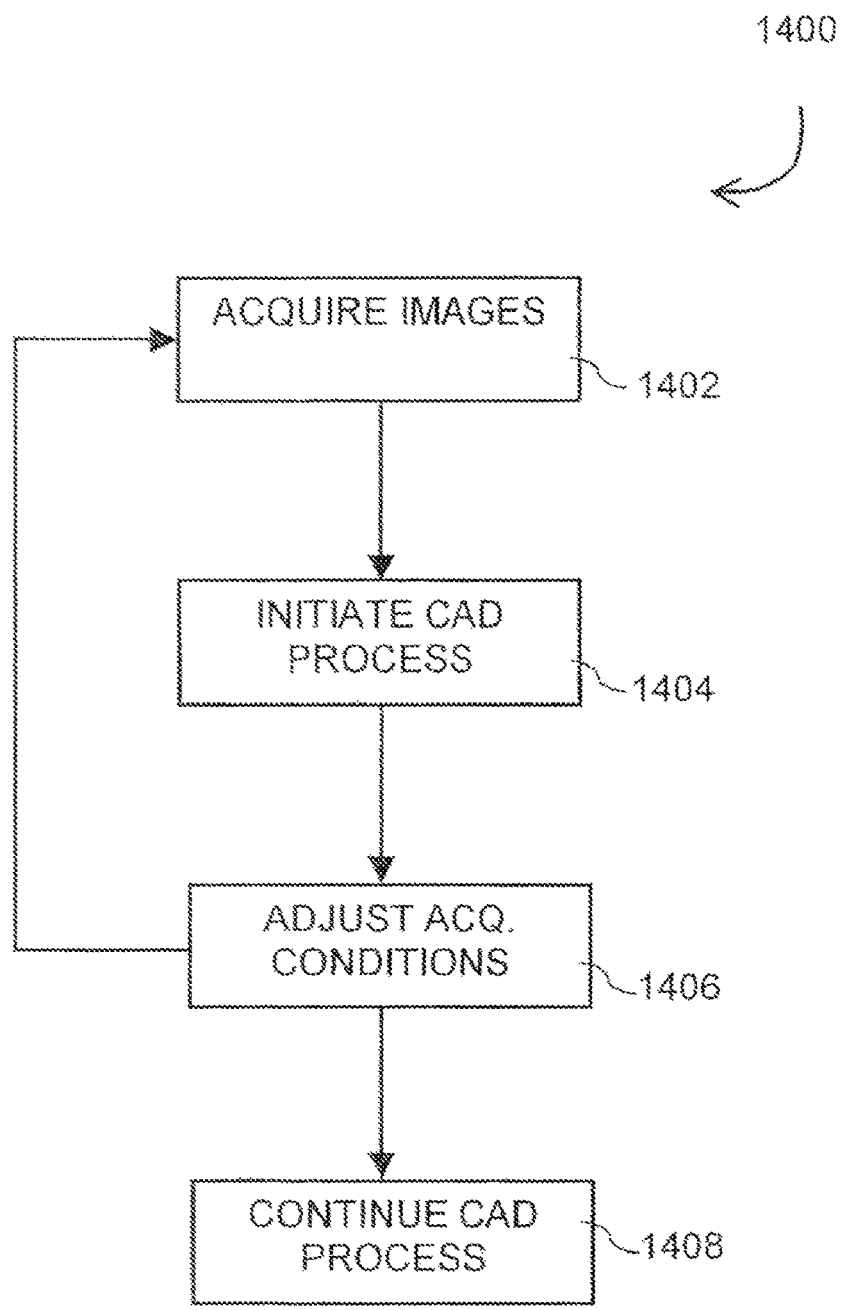
FIG. 14 shows schematically a process that an operator uses the CAD system shown in FIG. 12 to obtain optimal imaging results and make a diagnosis.

FIG. 14 is a flow chart summarizing the process 1400 described above for obtaining optimal images and then making a diagnosis based on the computed results produced by the CAD software system 130. Briefly, an operator initiates the process at step 1402 by acquiring images using a medical scanning device 104. Next, at step 1404, the operator initiates a CAD process to analyze the acquired image or images and extract and identify features relevant to a diagnosis. During the CAD process, the operator decides whether the image acquired is optimal, and adjusts accordingly image acquisition conditions, such as position and orientation of a transducer or positioning of the patient, at step 1406 in order to obtain optimal images. This process may be repeated until the operator is satisfied that optimal images are obtained. The operator then continues at step 1408 to make a diagnosis based on features identified and extracted from the optimal image as well as a diagnosis computed from the extracted features.

Variations to the process 1400 described is also possible. For example, real-time feedback may be provided during the process so that a user does not have to complete the CAD process on all images acquired. For example, each scan may produce a series of images, which may be displayed in a temporary window as a series of thumbnail images. As described above, the thumbnail images may all have different views of the same lesion automatically identified by the system, or may be the same initial image, with different lesions identified in each thumbnail images. Prior to proceeding further with steps 1404 to 1406, a user can select from the thumbnail images one or several images for further study and discard the remaining ones. Thus, instead of using the process 1400 for obtaining an optimal image, a user can also use a process modified from process 1400 for dynamically picking images for studying a particular suspect lesion or lesions.

As another example, the configuration shown in FIG. 12 also allows the operator to study the elasticity of a lesion, i.e., to acquire elastography images. To initiate the process, the operator starts by introducing some vibration into the region of tissues under examination. For example, the operator may apply some pressure to the tissues surrounding a lesion and then release the pressure. As will be appreciated, abnormal region such as a lesion or nodule may have different elasticity than its surrounding tissues. As the vibration is introduced into the tissue, elasticity of the abnormal region may be studied from the series of frames or images. As will be appreciated, an abnormal region may have different elasticity and therefore may respond differently to the vibration than the surrounding tissues. The series of images captured, once indexed as a time sequence, can be used to identify legions or nodules based on elasticity variations. In one implementation, the segmentation module utilizes these elasticity differences as identified from a series of frames to provide a better selection of segmentation candidate.

As a further example, in another implementation, the medical scanning device 104 shown in FIG. 12 is a Doppler imager. As will be appreciated, Doppler imaging is sensitive to blood flows in blood vessels. If a transducer applies too much pressure on the tissues thereby impeding blood flow inside the vessels, the image obtained may be of poor quality. The system provided by the configuration shown in FIG. 12 provides an immediate feedback, such as an audible alert to the operator, if the pressure applied by the transducer is too great. As part of the step of adjusting detecting and acquisition conditions, the operator may adjust the pressure of the transducer applied on a patient's skin, in order to obtain optimal Doppler images.

Various embodiments of the invention have now been described in detail. Those skilled in the art will appreciate that numerous modifications, adaptations and variations may be made to the embodiments without departing from the scope of the invention. Since changes in and or additions to the above-described best mode may be made without departing from the nature, spirit or scope of the invention, the invention is not to be limited to those details but only by the appended claims.

What is claimed is:

1. A system for providing interactive computer-aided detection of abnormalities captured in medical images, said system comprising:
an image processor, said image processor generating a boundary outline delineating a region within a medical image corresponding to a suspect lesion;
a user interface operative connected to said image processor, said user interface providing said boundary outline for user selection and modification and said image processor processing the medical image and extracting features relevant to diagnosing the abnormalities from the medical image, the extracted features satisfying descriptions of a set of pre-defined features and being associated with said region delineated by said selected boundary outline;
a decision engine for computing a computed diagnosis from the extracted features; and
an annotation and modification tool for a user to identify and modify a set of features within the medical image aided with the extracted features, said annotation and modification tool being operatively connected to said decision engine and providing the set of user identified features to the decision engine, and the decision engine being configured to re-compute the computed diagnosis from the set of user identified features upon receiving said set of user identified features.

2. The system of claim 1, further comprising a plurality of rules associating the set of pre-defined features with a range of possible diagnosis for the decision engine to compute the computed diagnosis from the extracted features.

3. The system of claim 2, wherein said plurality of rules are calibrated from a pool of diagnosed medical images.

4. The system of claim 1, further comprising a lesion locator for analyzing the medical image and identifying a region within the medical image corresponding to a suspect lesion.

5. The system of claim 1, wherein the image processor has a segmentation module for delineating one or more boundary outlines.

6. The system of claim 5, wherein the user interface is configured for displaying for user selection a plurality of alternative boundary outlines of the region corresponding to the suspect lesion and is responsive to a user indication for selecting one of the alternative boundary outlines as said selected boundary outline.

7. The system of claims 1, wherein said selected boundary outline has a set of control points modifiable by the user and, upon said set of control points being modified by the user, said image processor re-generates a modified boundary outline from said set of modified control points.

8. The system of claim 1, further comprising a report module for generating a report of findings based on the set of identified features and the established diagnosis.

9. A system for providing interactive computer-aided detection of abnormalities captured in a medical image, said system comprising:
- a graphical user interface for presenting the medical image to a user for review and modification;
- an input device for receiving user input;
- an image processing module for identifying image characteristics from the medical image, said image processing module being operatively connected to said graphical user interface;
- an annotation and modification tool for the user to modify said identified image characteristics; and
- a diagnosis decision engine operatively connected to said image processing module and said annotation and modification tool, said diagnosis decision engine having access to a set of pre-defined criteria, and being configured to compute an initial diagnosis from an initial set of image characteristics identified by said image processing module, and upon receiving from said annotation and modification tool a set of image characteristics modified by the user from the initial set of image characteristics, said diagnosis decision engine re-computing a diagnosis from said set of user modified image characteristics for user validation.

10. The system of claim 9, wherein said diagnosis is computed from a set of rules calibrated from a pool of diagnosed images.

11. The system of claim 9, further comprising a segmentation module for delineating one or more boundary outlines enclosing a region within the medical image corresponding to a suspect lesion, said one or more boundary outlines being displayed on said graphical user interface for user review and modification.

12. The system of claim 9, further comprising a lesion locator for analyzing the medical image and identifying a candidate region within the medical image corresponding to a suspect lesion, said candidate region being displayed on said graphical user interface for user selection, said image processing module identifying image characteristics associated with said candidate region.

13. A system for providing computer-aided diagnosis of abnormalities in a plurality of medical images, said plurality of medical images being different views of an anatomical region of a patient's body, said system comprising:
- an image acquisition module for acquiring said plurality of medical images;
- an image processor for processing each of said plurality of medical images and identifying an initial set of features within said each medical image relevant to diagnosing the abnormalities;
- a decision engine for computing an initial diagnosis from said plurality of said initial sets of identified features; and
- an annotation and modification tool for a user to modify said initial set of identified features to obtain a modified set of identified features;

wherein the decision engine re-computes a computed diagnosis for user validation from said modified set of identified features.

14. The system of claim 13, further comprising a lesion locator for analyzing the medical image and identifying a region within the medical image corresponding to a suspect lesion for selection by the user.

15. The system of claim 14, wherein said lesion locator identifies multiple regions within the medical image, each of said multiple regions corresponding to a lesion selected by the user.

16. The system of claim 15, wherein said initial set of identified features includes features associated with said each region of said multiple regions.

17. The system of claim 13, further comprising a report module for generating a diagnosis report upon validation of the computed diagnosis by the user.

18. The system of claim 17, wherein said diagnosis report includes identification information for auditing purposes.

19. The system of claim 18, wherein said identification information includes at least one of patient identification information, software identification information, examination identification, report serial number, time information relating to said diagnosis report, and user identification.

20. The system of claim 19, further comprising a cryptographic module for digitally signing said diagnosis report.

21. The system of claim 13, further comprising a template for generating a summary text based on said modified set of identified features and said computed diagnosis.

22. The system of claim 21, further comprising a pre-defined rule for associating said modified set of identified features and said computed diagnosis with a treatment recommendation, said treatment recommendation being modifiable by the user.

23. The system of claim 13, wherein said system is configured for processing said plurality of medical images obtained from multiple modalities.

24. The system of claim 23, wherein said initial sets of identified features include features associated with multiple regions in said each medical image.

25. The system of claim 24, wherein said computed diagnosis is computed from said modified set of identified features associated with said multiple regions in said each medical image.

26. The system of claim 23, wherein said multiple modalities include at least two of sonographic images, Doppler images, spectral Doppler images, X-ray images, CT images, PET images, PET-CT images and MRI images.

27. A method of providing interactive computer-aided detection of abnormalities captured in a medical image, said method comprising the steps of:
- obtaining a digitized medical image;
- processing said digitized medical image to identify an initial set of image features within said digitized medical image, said initial set of identified image features satisfying descriptions of a set of pre-defined characteristics;
- presenting said initial set of identified image features on a graphical user interface for user review and modification;
- receiving a modified set of image features modified by a user from said initial set of identified image features;
- a decision engine computing a diagnosis from said modified set of image features;
- if said diagnosis is not validated by the user, receiving further modification to said modified set of image features from the user, providing said further modified set of image features to the decision engine and the decision engine re-computing said diagnosis from said further modified set of image features until said diagnosis is validated by the user; and
- upon said diagnosis being validated by the user, producing a diagnosis report based on said diagnosis.

28. The method of claim 27, further comprising the steps of:
- prior to processing said digitized medical image, receiving an identification of a region of interest in said digitized medical image from a user;

generating a plurality of segmentation candidates, each segmentation candidate corresponding to an alternative boundary outline delineating said region of interest;
providing said plurality of segmentation candidates to the user for user selection;
wherein said processing step utilizes a selected segmentation candidate when identifying the set of image features.

29. The method of claim 27, further comprising the step of obtaining a plurality of rules associating the set of pre-defined characteristics with possible diagnosis, said diagnosis being computed from said plurality of rules and said modified set of image features.

30. The system of claim 29, wherein said plurality of rules are calibrated from a pool of diagnosed medical images.

31. A method of acquiring a medical image aided by a computer-aided detection system, said computer-aided detection system having a medical imaging device for generating a medical image and an analytic engine for processing the medical image, the method comprising the steps of:

acquiring one or more medical images directly from a patient using the medical imaging device,
analyzing said one or more medical images using said, analytic engine;
adjusting acquisition conditions of said medical imaging device based on results of processing said one or more medical images; and
acquiring an optimal image using said medical imaging device directly from said patient.

32. The method of claim 31, wherein the step of analyzing each of said plurality of medical images includes extracting features within said each medical image relevant to diagnosing a disease and generating a computed diagnosis from the extracted features.

33. The method of claim 31, wherein the steps of acquiring a plurality of medical images and analyzing the plurality of medical images are performed in same examination session.

* * * * *